US012789168B2

(12) United States Patent
Boschini et al.

(10) Patent No.: US 12,789,168 B2
(45) Date of Patent: Nov. 10, 2026

(54) PREPARATION OF MAGNETIC CORE-SHELL PARTICLES

(71) Applicant: Université de Liège, Liège (BE)

(72) Inventors: Frédéric Boschini, Rocourt (BE); Jérôme Bodart, Ougrée (BE); Rudi Cloots, Hélécine (BE)

(73) Assignee: Université de Liège, Liège (BE)

( * ) Notice: Subject to any disclaimer, the term of this patent is extended or adjusted under 35 U.S.C. 154(b) by 846 days.

(21) Appl. No.: 17/906,787

(22) PCT Filed: Mar. 30, 2021

(86) PCT No.: PCT/EP2021/058352
§ 371 (c)(1),
(2) Date: Sep. 20, 2022

(87) PCT Pub. No.: WO2021/198289
PCT Pub. Date: Oct. 7, 2021

(65) Prior Publication Data

US 2023/0127156 A1 Apr. 27, 2023

Related U.S. Application Data

(60) Provisional application No. 63/001,680, filed on Mar. 30, 2020.

(30) Foreign Application Priority Data

Dec. 17, 2020 (EP) .................................... 20214855

(51) Int. Cl.

| | |
|---|---|
| ***B01J 20/32*** | (2006.01) |
| ***B01J 20/06*** | (2006.01) |
| ***B01J 20/10*** | (2006.01) |
| ***B01J 20/28*** | (2006.01) |
| ***C12N 15/10*** | (2006.01) |

(52) U.S. Cl.

CPC ........... *B01J 20/3293* (2013.01); *B01J 20/06* (2013.01); *B01J 20/103* (2013.01); *B01J 20/28009* (2013.01); *B01J 20/28011* (2013.01); *B01J 20/28019* (2013.01); *B01J 20/28059* (2013.01); *B01J 20/28061* (2013.01); *B01J 20/3236* (2013.01); *C12N 15/1013* (2013.01); *B01J 2220/46* (2013.01); *B01J 2220/4806* (2013.01); *B01J 2220/4812* (2013.01)

(58) Field of Classification Search

CPC ...... B01J 20/3293; B01J 20/06; B01J 20/103; B01J 20/28009; B01J 20/28011; B01J 20/28019; B01J 20/28059; B01J 20/28061; C12N 15/1013

See application file for complete search history.

(56) References Cited

U.S. PATENT DOCUMENTS

2004/0014070 A1 1/2004 Pinsl-Ober et al.

FOREIGN PATENT DOCUMENTS

| | | | | |
|---|---|---|---|---|
| DE | 19855259 A1 * | 5/2000 | ............. | B82Y 25/00 |
| EP | 1154443 A1 | 11/2001 | | |
| WO | WO-2008058996 A2 * | 5/2008 | ............. | B82Y 25/00 |
| WO | 2011013169 A1 | 2/2011 | | |
| WO | 2014090838 A1 | 6/2014 | | |

OTHER PUBLICATIONS

Khosroshahi, M. E., and L. Ghazanfari. "Preparation and characterization of silica-coated iron-oxide bionanoparticles under N2 gas." Physica E: Low-dimensional Systems and Nanostructures 42.6 (2010): 1824-1829. (Year: 2010).*

* cited by examiner

*Primary Examiner* — Bao-Thuy L Nguyen
*Assistant Examiner* — Christopher Evans
(74) *Attorney, Agent, or Firm* — Banner & Witcoff, Ltd.

(57) ABSTRACT

The invention relates to a process for preparing core-shell particles comprising the steps of (i) providing a dispersion of primary magnetic particles having a mean diameter lower than 200 nm in a solvent; (ii) adding one or more (semi-)metal (oxyhydr)oxide(s) and/or one or more precursor(s) of a (semi-)metal (oxyhydr)oxide to said dispersion; (iii) optionally adding a hydrolysis agent for said one or more precursor(s); (iv) injecting the dispersion in a spray dryer; whereby a (semi-)metal (oxyhydr)oxide shell is formed on the magnetic particles during spray drying. The invention also relates to particles obtainable by said process, to a formulation of said particles in a solvent and to the use of said particles or said formulation for RNA or DNA extraction.

14 Claims, 23 Drawing Sheets

PREPARATION OF MAGNETIC CORE-SHELL PARTICLES

RELATED APPLICATIONS

This application is a National Stage Application under 35 U.S.C. 371 of co-pending PCT application PCT/EP2021/058352 designating the United States and filed Mar. 30, 2021; which claims the benefit of U.S. application No. 63/001,680 and filed Mar. 30, 2020, and EP Application Serial No. 20214855.7 and filed Dec. 17, 2020, each of which are hereby incorporated by reference in their entireties.

TECHNICAL FIELD OF THE INVENTION

The present invention relates to a process for preparing core-shell particles, the particles obtained by the process, the suspensions of such particles and the use thereof.

BACKGROUND OF THE INVENTION

In the last years, lots of research focused on the use of core-shell particles with $Fe_3O_4$ as a core for DNA or RNA extraction or purification. Due to the low toxicity and magnetism properties, $Fe_3O_4$ particles are good candidates in biotechnology for extracting RNA from viruses. However, in this kind of application, $Fe_3O_4$ particles have to be functionalized with specific coatings such as glass or silica. Several synthesis routes have been developed to produce core-shell particles with controlled surface properties. The Stober process is an interesting way to prepare colloidal silica particles. Tetraethyl orthosilicate (TEOS) is used as a reagent therefore. TEOS can be hydrolyzed and condensed in an alcohol-water system using ammonia as catalyst. If this process is applied in the presence of nanometric particles in suspension, a silica coating is formed onto these nanoparticles (Lu et al., Colloids and Surfaces A: Physicochem. Eng. Aspects 317, 2008, p450; Sharafi et al., Iran J Pharm Res, 2018 Winter; 17, p386). A similar process is disclosed in EP0757106A2 by Uematsu et al.

This process can be used to synthetize core-shell particles of $Fe_3O_4$ coated by $SiO_2$. However, this wet process presents several problems. Firstly, it requires the use of large quantities of solvent. Secondly, it requires a long reaction time, of between 4 to 24 hours depending on the thickness of the shell desired. Thirdly, several parameters such as reactant concentration, stirring speed, type of stirring, reaction temperature can influence the quality of the coating and the aggregation of particles during the process. Hence the process control is always difficult and the process must be carefully monitored to avoid any deviation in the final product. Moreover, after reaction the fresh core-shell particles have to be intensively washed with organic solvent to remove the unhydrolyzed TEOS and with abundant water to remove the excess of colloidal silica particles in the suspension and/or the TEOS which were not used for the coating of the particles. Finally, after the drying step, purified core-shell particles must be dried by lyophilization to avoid their oxidation. Hence, the wet process is a long process with multiple steps. It is not convenient for a large scale production of core-shell particles.

A spray drying process was disclosed by Roche Diagnostics in WO 01/37291 A1 to prepare magnetic glass particles. However, a sintering step is necessary to obtain such particles. The document discloses a sinter temperature of around 750° C. This step is energy-consuming and impedes a rapid and efficient process for the synthesis of large quantities of core-shell particles.

It is an aim of the present invention to solve or alleviate one or more of the above-mentioned problems. The present invention particularly seeks to provide a process to prepare core-shell particles in a more efficient way, without any washing step and/or purification step and/or sintering step. The present invention enables to prepare large quantities of magnetic particles in a reduced period of time.

DESCRIPTION OF THE INVENTION

The inventors of the present invention have now found a process meeting these needs.

According to one aspect of the present invention, a process for preparing core-shell particles is provided, comprising the steps of i. providing a dispersion of primary magnetic particles having a mean diameter lower than 200 nm in a solvent, ii. adding one or more (semi-)metal (oxyhydr)oxide(s) and/or one or more precursor(s) of a (semi-)metal (oxyhydr)oxide to said dispersion, iii. optionally adding a hydrolysis agent for said one or more precursor(s), iv. injecting the dispersion in a spray dryer, whereby a (semi-)metal (oxyhydr)oxide shell is formed on the magnetic particles during spray drying.

Advantageously, the process is a one step process. By a one step process is meant that the spray drying step is sufficient to obtain a powder of magnetic particles covered by a (semi-)metal (oxyhydr)oxide shell. After such powder recovery, no supplementary step is needed. Advantageously, the process does not comprise a sintering step. Advantageously, the process does not comprise a washing step. Indeed, there is no washing of (semi-)metal (oxyhydr)oxide-coated magnetic particles required at the end of the process as for conventional wet process.

It is also an advantage that the process is reproducible. A higher reproducibility of the process was demonstrated because the core-shell particles are formed during the drying step and not in solution as for conventional wet process (sol-gel) or in a further treatment as a calcination step.

It is a further advantage that the process is easy to implement. By easy is meant that the parameters are relatively easy to control. The process is versatile. It allows to work at different inlet temperatures and different pressures as will be detailed hereafter.

It is a further advantage that the process may be a continuous process. By a continuous process, one means that the dispersion containing primary magnetic particles and a (semi-)metal (oxyhydr)oxide or a precursor thereof may be injected continuously in the spray dryer and hence the powder of (semi-)metal (oxyhydr)oxide-coated magnetic particles may be recovered continuously. This enables to obtain large quantities of products.

According to a preferred embodiment of the present invention, a (semi-)metal oxyhydr(oxide) used in step (ii) is silica and/or at least one silica precursor whereby a silica shell is formed on the magnetic particles during spray drying.

According to an embodiment of the present invention a combination of more than one (semi-)metal oxyhydr(oxide) or precursors thereof is used in step (ii) of the process of the invention. Silicon oxide, also referred to as silica, may thus be used in combination with any of another (semi-)metal (oxyhydr)oxide. Alternatively, any (semi-)metal (oxy)hydroxide may be combined with any of a second (semi-)metal (oxyhydr)oxide. Hence a combination of two or more (semi-)metal (oxyhydr)oxide (including silica or not including silica) may be advantageous. Such combination may lead to in situ reaction inside the spray dryer. Such in situ reaction may lead to the formation of a tertiary phase.

It will be understood by the person skilled in the art that the choice of (semi-)metal (oxyhydr)oxide(s) may be guided by their properties such as for example the well-known catalytic properties in case of titanium dioxide.

For all (semi-)metal (oxyhydr)oxides used in the process of the present invention, including silica, a common property is the ability to form hydrogen-bonds. This property is particularly advantageous when such a (semi-)metal (oxyhydr)oxide is present on the surface of a particle, as in the process of the invention. More specifically when such coated particles have not undergone a sintering step.

It is a further advantage that the primary magnetic particles in the dispersion have a nanometric size, such as a mean diameter below 200 nm. Preferably, the mean diameter of the primary magnetic particles is below 100 nm. The primary magnetic particles may for example have a size between 10 and 80 nm. A mean diameter is an average diameter or average section of the particles as measured on a representative sample of particles. The size of the particles may be measured by electronic microscopy, such as transmission electron microscopy (TEM) or scanning electron microscopy (SEM) or by dynamic light scattering (DLS) or by granulometry. Preferably the size is measured by DLS, which also gives an indication of particle size distribution. Smaller particles have the advantage of offering a larger specific surface area. It also favours the attachment of silica or of another (semi-)metal (oxyhydr)oxide such as alumina (aluminum oxide) or titania (titanium dioxide) or zirconia (zirconium oxide) or pseudoboehmite (AlO(OH)) or zinc oxide to the magnetic core during spray drying. Smaller particles also enable to obtain a more homogeneous coating on the magnetic core. A small size is also preferred to ensure a magnetic core to the core-shell particles. In the case of iron oxide particles, if sufficiently small, they can respond to a magnetic field with superparamagnetism.

Preferably, step (iii) of optionally adding a hydrolysis agent is included when the one or more precursor(s) has a hydrolysis rate that is too low to enable the hydrolysis to start in absence of such a hydrolysis agent. For example, in case of a silica precursor, the precursor contains silicate bonds such as tetraalkyl orthosilicate that needs to be hydrolysed to form silica or $SiO_2$. In case of titanium isopropoxide as precursor, the hydrolysis rate is high enough to enable the hydrolysis to start in the presence of an organic solvent such as an alcohol solvent, as will be detailed in the examples. The hydrolysis agent may be added either to the dispersion or may be added as a separate injection to the spray dryer concomitantly. The latter is a further advantage to the continuous character of the process. Preferably the tubes of the separate injections meet such as with a static mixer, before entering the spray dryer and hence the hydrolysis starts just before entering the spray dryer.

Preferably, the primary magnetic particles are iron oxide particles, in particular $Fe_3O_4$.

Advantageously, $Fe_3O_4$ particles are used as core material due to their magnetic properties. Their magnetic properties enable their extraction from a liquid using a magnet, such as a commercial magnet. Other magnetic materials are suitable, such as $Fe_2O_3$ or other ferromagnetic or ferrimagnetic materials.

Preferably, the weight ratio of iron oxide to the combined amount of (semi-)metal (oxyhydr)oxide(s) in the dispersion is from 0.1:5 to 5:0.1, preferably from 0.5:2 to 2:0.5 (e.g. $Fe_3O_4$:$SiO_2$). This ratio concerns the formulation of the precursors solution.

It is an advantage of the process that it enables a control of the thickness of the shell by adjusting the ratio of primary magnetic particles to the one or more (semi-)metal (oxyhydr)oxide(s) in the dispersion, before injecting the dispersion in the spray dryer. A preferred weight ratio may be from 0.1:5 to 5:0.1, preferably from 0.1:2 to 2:0.1, preferably from 0.5:2 to 2:0.5, more preferably from 0.3:1 to 3:1. A suitable ratio for the use of core-shell particles to extract RNA is a ratio of 1:1. The weight ratio is calculated by weighting the agents (such as for example iron oxide and silica or silica precursor) before mixing, taking into account the concentration of the dispersion. At the end of the process, an atomic ratio may be calculated by performing an energy dispersive X-ray (EDX) analysis. The thickness of the shell formed may be evaluated through electronic microscopy. It may be from 0.1 nanometer to 500 nanometers, preferably from 1 nanometer to 100 nanometers. A suitable thickness evaluated by transmission electronic microscopy (TEM) is for example 20 nm. A thicker shell may be obtained with a higher concentration of (semi-)metal (oxyhydr)oxide or of precursor(s) thereof.

Preferably, the solvent provided for the dispersion of primary magnetic particles is water or is a solvent miscible with water such as methanol, ethanol, butanol, isopropanol, acetonitrile, ethyl acetate, diethylether, acetone or propanal, used alone or in combination.

The miscibility with water advantageously enables to form a homogenous solution without any precipitates. Advantageously, the mixture of solvent and water may lead to an azeotrope solution formation with a boiling point lower than 130° C. Preferably, the solvent is a polar solvent. Preferred solvents may include ethanol or isopropanol.

According to a preferred embodiment of the present invention in step (ii) solely silica and/or a silica precursor is used. Preferably, the silica and/or silica precursor is a tetraalkyl orthosilicate, colloidal silica or a mixture of both.

Tetraethyl orthosilicate (TEOS) is an example of a suitable silica precursor. It is a well-known precursor of silica in sol-gel processes. Silica can be formed by hydrolysis. Hydrolysis may be done in acid or basic conditions.

An example of a suitable hydrolysis agent particularly for TEOS in acidic conditions may be acetic acid. An example of a suitable hydrolysis agent in basic conditions, in particular for TEOS, may be an aqueous solution of ammonium. In particular, TEOS is first hydrolyzed with water to produce silanol, a molecular unit which can condensate to form siloxane bridges between such molecular units which is finally transformed in gel ($SiO_2$ or $SiO(OH)_2$) during the fast drying step.

The silica precursor may influence the morphology of the silica-coated magnetic particles. For example, adjusting the weight ratio of TEOS to colloidal silica in the dispersion may enable a control of the morphology of the silica-coated particles.

Preferably, the (semi-)metal in the (semi-)metal(oxyhydr) oxide is a (semi-)metal from group IIIA, IVA or IVB of the Periodic Table of Elements, preferably Si, Ti, Zr or Al. Preferably the one or more (semi-)metal (oxyhydr)oxide(s) is selected from the list of silica, titanium oxide, aluminum oxide, zirconium oxide, pseudoboehmite, zinc oxide.

Preferably, the hydrolysis agent is an aqueous solution of a gaseous base.

It is an advantage of using a gaseous agent as it may evaporate during spray drying and is not recovered in the final product. An example of suitable hydrolysis agent is ammonia. It is an advantage to perform the process under basic conditions to avoid any oxidation of the particles. By basic conditions one means a pH of above 7. The hydrolysis may also be performed under slightly acidic conditions. Preferred pH ranges are between 4 and 14.

Preferably, step (iv) is performed immediately after step (ii) or, when a hydrolysis agent is present, immediately after (iii).

It is an advantage of the process that it can be a very fast process. This is because no ageing time is required before the injection of the feed stock suspension in the spray dryer, in contrast to the conventional wet process (such as by sol-gel).

It is an advantage of the process that a very short ageing time or even no ageing time favours a high yield of recovery of particles. A suitable duration between step (ii) or step (iii) and step (iv) may be from a few seconds to about 10 minutes, more preferably from 5 seconds to 2 minutes, even more preferably 30 seconds. A typical duration between step (ii) or step (iii) and step (iv) is 30 seconds.

Preferably, the pressure of the spray dryer is about 1 bar.

Preferably the pressure is low enough to ensure a high yield of recovery of the product. A pressure between 0.5 and 3 bar enables to optimize the size of the particles in the spray dryer.

Preferably, the outlet temperature of the spray dryer is between 50° C. and 150° C.

Advantageously the outlet temperature is set to evaporate any solvent. Advantageously the outlet temperature is below 150° C., more preferably below 130° C. even more preferably below 100° C. to avoid any waste of energy Preferably, the process further includes a step (v) of recovering a powder of magnetic particles coated by (semi-) metal (oxyhydr)oxide from an outlet of the spray dryer through magnetization.

It is an advantage of the process that the powder may be recovered through magnetization and be ready for use. Such a type of recovery enables to collect magnetic particles only and leaves (semi-)metal (oxyhydr)oxide(s) or any precursor (s) thereof that is unattached to the magnetic core aside. Hence, such a type of recovery is playing the role of purification of the final product. It is a further advantage of the magnetic recovery that the powder is collected more easily and enables a higher yield of production. Any type of magnet may be used to collect the powder. Preferably a magnet is used such as one with an adhesive force value of 500 N. Yields may be from 60%, preferably from 70%, even more preferably from 80%.

Preferably, the process further includes a preliminary step (prior to step (i)) of ball-milling a suspension of primary magnetic particles in a solvent to obtain particles of suitable size. Such a step enables to obtain a very homogeneous dispersion of primary particles having a reduced size. Alternatively, a feed stock suspension of particles is used directly in the process.

According to a second aspect, particles obtainable by the process of the invention are provided.

It is an advantage of the process that a relatively pure product may be obtained, as explained above. When recovered through magnetization, only particles with a magnetic core are collected. Hence, (semi-)metal (oxyhydr)oxide not attached to a magnetic particle will not be recovered. Also, through the process of the invention, by-products can only be solvents such as water and alcohol and which are evaporated at the outlet.

It is also an advantage that the product obtained is easy to handle, as a dry powder is obtained. This is contrary to conventional wet processes.

It is a further advantage that the product provides a high homogeneity of the (semi-)metal (oxyhydr)oxide coating onto the magnetic particles, this means that the coating is dispersed around the particle with the same thickness. This is ensured thanks to the formation of the shell during spray drying and not during a preliminary step as in prior art methods. The homogeneity of the shell may for example be observed by electron microscopy.

It is yet a further advantage that the product may have a versatile morphology. The process enables to modify the morphology of the (semi-)metal (oxyhydr)oxide-coated magnetic particles by for example adjusting the weight ratio of (semi-)metal (oxyhydr)oxide or precursors thereof in the dispersion before spray drying. The process enables to obtain particles with different possible morphology of the particles, such as a porous morphology, a spongeous-like morphology, a morphology with open or closed pores. The size of the pores may also be tunable.

Furthermore, it is an advantage of the process that the size of the particles may be controlled and tuned. The process also allows for a good control of the granulometry of the particles.

Preferably, the obtained core-shell particles have a density of less than 0.5 g/ml.

Advantageously particles obtained by the process of present invention have a very low density compared to existing core-shell particles. Preferably the density is less than 0.5 g/ml, more preferably below 0.2 g/ml, even more preferably below 0.1 g/ml. The advantage of a low density is that the particles have a higher active surface and hence a higher surface exchange. It is also an advantage in that the sedimentation rate of the particles in suspension is reduced.

Preferably, the obtained core-shell particles have specific surface area of at least 30 $m^2/g$.

It is advantageous that the core-shell particles have a high specific surface area to favour interaction with an external agent during use, such as an interaction with RNA or DNA. Such specific surface area may be, for example, measured by adsorption such as through BET (Brunauer-Emmett-Teller). A preferred specific surface area is of at least 40 $m^2/g$.

Preferably, the obtained core-shell particles have an open-pore morphology.

The morphology of the particles obtained by the process may be spherical or pseudospherical or spongeous-like. Advantageously, the particles may have a porous structure. Preferably, the particles may have an open-pore structure, which is advantageous to favour interaction with the liquid in any application wherein the particles are used to extract material from a liquid.

Advantageously, the obtained core-shell particles have a high content of (semi-)metal, such as for example a high content of Si, such as an atomic weight ratio of (semi-)metal of above 10%. In the preferred case of Si, the atomic weight ratio is of above 20%. The atomic weight ratio may be measured by EDX analysis on the powder collected from the spray dryer.

According to a third aspect, there is provided a formulation of the core-shell particles in a solvent.

Advantageously, the particles are formulated in a solvent wherein the particles may be homogeneously dispersed, such as under stirring for example. The solvent may be an alcohol or a mixture of alcohol and water. The loading of the core-shell particles in the formulation may be between 0.5 and 15 wt %. It is an advantage that the loading of core-shell particles in the formulation is relatively low with still good properties (such as the capacity of interaction with RNA or DNA) achieved. This may be due to the low density and/or the high specific surface area of the core-shell particles.

It is a further advantage that the formulation is stable, without the need to add a stabilizer. Stable means that the formulation can be used several days and even several months after being prepared.

According to a fourth aspect, there is provided the use of particles obtained according to the invention or of a formulation of such particles according to the invention for RNA or DNA extraction.

It is an advantage of the invention that particles obtained are particularly well suited for use for RNA or DNA extraction. Particles containing a (semi-)metal (oxyhydr) oxide shell have the ability to form hydrogen bonds with DNA or RNA in suitable conditions of ionic strength and pH of the medium. It was shown that, for example, the silica-coated magnetic particles have a high sensitivity for DNA and RNA extraction. By high sensitivity, one means a CT value between 15 and 30, preferably between 23 and 26.

It is a further advantage that the functionalities of the core and the shell may be combined and hence enable various applications. In particular, the magnetic properties of the core may be advantageously combined with the possibility of functionalization of the surface of the shell, such as for example the silica shell. The shell may be functionalized, for example by a chemical modification as known in the art. The magnetic properties of the core may also be modulated. The (semi-)metal (oxyhydr)oxide coating, chemically modifiable, also advantageously has a protective effect on the core and renders the magnetic core highly stable and/or non oxidable in different environments.

Thanks to the magnetic properties of the core and to the relatively easy and versatile functionalization of the shell, applications may be found in the pharmaceutical and medical field such as targeted drug delivery systems (a way for increasing the concentration of drug in some parts of the body), therapy with a magnetic field such as hyperthermia therapy induced by AC (alternative current) magnetic field (a way of selective thermal destruction of transformed cells without causing damage of healthy cells), targeted photodynamic therapy (associated with a specific functionalization of the e.g. silica shell via a photosensitizer), immobilization, purification and separation of biological entities such as proteins, enzymes, antibodies, . . . . Applications may also be found in the environmental field such as the removal of pollutants from the environment.

DESCRIPTION OF ILLUSTRATIVE EMBODIMENTS

By magnetic particles, one means particles owing magnetic properties. One also means magnetizable particles.

By primary particles, one means particles before the spray drying process.

By a dispersion, one means a homogeneous distribution of particles in a liquid, meaning that the particles are well dispersed in a liquid, meaning that the same amount of particles can be provided from any sample of the suspension. By dispersion one also means a suspension and vice-versa. With a homogeneous distribution of the particles, is also meant a narrow distribution size of nanoparticles in suspension in the solvent, such as a distribution size wherein at least 50% of the particles have a size differing by less than 100 nanometers, preferably less than 50 nanometers. Particle size distribution may be measured by DLS. Such a dispersion of nanoparticles is also stable. By contrast, a broad particle distribution size leads to the sedimentation of the larger particles.

By silica precursor one means any molecules which can form $SiO_2$.

By silica shell, one means a shell formed of $Si—O_{2-x}(OH)_{2x}$ with x being comprised between 0 and 2. Hence, the shell may comprise only $SiO_2$ groups but also partly $Si(OH)_4$ and/or partly $SiO(OH)_2$. This is because there is no calcination step in the process, allowing the presence of —OH groups to remain at the surface.

By (semi-)metal (oxyhydr)oxide, one means a metal oxide or a semi-metal oxide or a metal oxyhydroxide or a semi-metal oxyhydroxide or a combination of two or more of these. A (semi-)metal (oxyhydr)oxide according to the invention has the property of forming hydrogen-bonds in suitable conditions. For example, a metal oxide may be titanium oxide (also referred to as titania or $TiO_2$) or aluminum oxide (also referred to as alumina or $Al_2O_3$) or zirconium oxide (also referred to as zirconia or $ZrO_2$). For example, a metal oxyhydroxide may be pseudoboemite also referred to as boehmite or AlO(OH).

By (semi-)metal (oxyhydr)oxide shell, one means a shell or coating formed of one or more (semi-)metal (oxyhydr) oxide(s).

By (semi-)metal (oxyhydr)oxide precursor, one means any precursor that is able to lead to a (semi-)metal (oxyhydr) oxide under conditions of pressure and temperature that are compatible with a spray dryer.

The process of the present invention may generally involve the following steps:

A powder of magnetic particles, such as an iron oxide powder, is dispersed in a solvent to produce a dispersion or suspension of iron oxide particles. The dispersion may be enhanced if needed by any means, such as by mechanic stirring or by using an ultrasonic probe. Optionally a dispersing agent may be added. These particles in suspension will be the core of the final particles. To this suspension, a solution of (semi-)metal (oxyhydr)oxide or precursor(s) thereof is added generally under agitation to obtain a homogeneous suspension. To this feed stock suspension, a basic solution, i.e. the hydrolysis agent, may be added under stirring to favour the homogenization. The mixed slurry is subsequently dried by a spray drying method to produce core-shell particles in a one step process.

The process is suitable to obtain silica-coated magnetic particles but also magnetic particles covered by ceramic powders or other (semi-)metal (oxyhydr)oxide. Suitable oxides forming a shell on the magnetic particles include silica ($SiO_2$), alumina ($Al_2O_3$), pseudoboehmite (AlO(OH), titania ($TiO_2$), zirconium oxide ($ZrO_2$).

In embodiments, $Fe_3O_4$ particles are used as core material due to their magnetic properties. Their magnetic properties enable their extraction from liquid using a magnet, such as a commercial magnet. Other magnetic materials such as $\gamma Fe_2O_3$ or ferro- or ferrimagnetic materials or FeO. $Fe_3O_4$, AlNiCo, $SmCo_5$, $Sm_2Co_{17}$, $Nd_2Fe_{14}B$ could be used for this application of DNA or RNA extraction.

In embodiments, $Fe_3O_4$ particles used in the process may have an average size below 200 nm and more preferably below 100 nm. Even more preferably, the iron oxide particles have a size between 10 and 80 nm. Smaller particles have the advantage of offering a larger specific surface area. The size is also important to ensure a magnetic core to the core-shell particles.

Smaller particles and stable dispersion of nanoparticles can be obtained either by a previous grinding process of commercially available particles or by their previous synthesis by coprecipitation.

In embodiments, the silica shell is created by using a tetraalkyl orthosilicate solution, for example, a tetraethyl orthosilicate (TEOS) solution or colloidal silica or a mixture of both. The use of TEOS or colloidal silica or a mixture of both may influence the shape of the core-shell particles obtained. Other possible silica precursors include silicic acid, orthosilicic acid, pyrosilicic acid, metasilicic acid, disilisic acid, fluosilicic acid, tetramethylammonium silicate, tetramethyl orthosilicate, tetraethyl orthosilicate, tetrapropyl orthosilicate, tetrabutyl orthosilicate, tetrapentyl orthosilicate, tetrahexyl orthosilicate.

In an alternative embodiment, core-shell particles may be prepared according to the process of the invention with a titania shell. In such a case, suitable precursor of titania may include tetra alkyl orthotitanate (alkyl=methyl, ethyl, propyl, butyl, pentyl, hexyl, . . . ), titanium alkoxide (alkyl=methyl, ethyl, propyl, isopropyl, butyl, tertbutyl, ethylhexyl, . . . ), titanium diisopropoxide bis(acetylacetonate), titanium (IV) (triethanolaminato)isopropoxide, titanium(IV) 2-ethylhexyloxide.

In an alternative embodiment, core-shell particles may be prepared according to the process of the invention with an alumina ($Al_2O_3$) or pseudoboehmite (AlO(OH) shell. In such a case, suitable precursors are aluminum acetylacetonate, aluminum hydroxide, boehmite, alumina, . . . .

In an alternative embodiment, core-shell particles may be prepared according to the process of the invention with a zirconia ($ZrO_2$) shell. In such a case, suitable precursors are zirconium(IV) 2-ethylhexanoate, zirconium(IV) acetate hydroxide, zirconium(IV) acetylacetonate, zirconium(IV) butoxide, zirconium(IV) carbonate, zirconium(IV) carbonate hydroxide oxide, zirconium(IV) ethoxide, zirconium(IV) hydroxide, zirconium(IV) isopropoxide, zirconium(IV) propoxide, zirconium acrylate, zirconium carboxyethyl acrylate, zirconium tetrakis(2,2,6,6-tetramethyl-3,5-heptanedionate), zirconium(IV) 2-ethylhexanoate, zirconium (IV) tert-butoxide, ammonium zirconium(IV) carbonate.

In an alternative embodiment, core-shell particles may be prepared according to the process of the invention with a zinc oxide (ZnO) shell. In such a case, suitable precursors are zinc hydroxide, zinc carbonate, zinc acetate, zinc nitrate, zinc sulfate, diethylzinc, zinc methoxide, zinc acetate, zinc acrylate, zinc methacrylate, zinc neodecanoate, zinc picolinate, zinc salicylate, zinc stearate, zinc undecylenate, zinc propionate, zinc citrate, zinc diethyldithiocarbamate, zinc dimethyldithiocarbamate, zinc carbonate basic.

In embodiments when a silica precursor such as TEOS solution is used, a basic solution is added to promote hydrolysis and the shell formation. A basic solution may increase the pH of the suspension to a pH of about 9. The presence of TEOS in presence of colloidal silica may advantageously improve the adhesion of silica nanoparticles in the shell to avoid their release when core-shell particles are put in suspension.

In embodiments, to avoid any washing of the core-shell powder after production and to produce a ready-to-use powder, substances used to promote hydrolysis of silica precursors such as TEOS in basic conditions may evaporate during the spray drying step. Preferably, ammonia is used as the basic solution or a precursor of ammonia or tetramethyl ammonium hydroxide. Other bases with a boiling point superior to the inlet or outlet temperature of the spray dryer may be used.

In embodiments, colloidal silica may have a size below 100 nm to produce shell with high specific surface area. A specific surface area may be from 30 $m^2/g$ up to 120 $m^2/g$.

In embodiments, colloidal silica may have a size at least lower than two times the size of $Fe_3O_4$ particles to guarantee the encapsulation of $Fe_3O_4$ particles during the spray drying process.

In a spray dryer, a solution or dispersion or suspension is sprayed into droplets and the solvent or liquid in each droplet is evaporated by a hot gas flow (which may be air or another gas like nitrogen or argon or a combination of both), resulting in a dry powder. Larger quantities can therefore be obtained simply by spraying a larger volume over a longer time, or even continuously without modification of the conditions experienced by each individual droplet. Spray drying can be applied to suspensions or dispersions or solutions but also to the intermediate case of suspensions in solutions. In all of these cases it can be used as a shaping technique, typically to obtain spherical granules.

In embodiments, spray-drying of the dispersion can be directly performed after the addition of the basic solution to the dispersion without any ageing time.

In embodiments, spray-drying of the dispersion may be performed by nebulizing it in a spray dryer with an outlet temperature lower than 130° C.

In embodiments, in order to highly improve the recovery of the core-shell particles at the end of the process, magnets may be put inside and/or outside of the recovery bowl. This will favour the sticking of the core-shell particles on the wall and in the bottom of the bowl.

In embodiments, the core-shell particles may have a size of about 1 to 20 μm.

The obtained powder has a flaky-like aspect, with particles tending to be linked one to another. The powder may be kept under an inert atmosphere before use, although the powder is usually not subjected to oxidation thanks to the homogeneous (semi-)metal (oxyhydro)oxide (such as $SiO_2$) coating.

The powder may subsequently be used as a formulation or dispersion or suspension in a solvent, such as isopropanol. A concentration of such formulation may be for example 15 g/L. In such a dispersion, the sedimentation rate may be high. Particles may be dispersed again through simple stirring.

The core-shell magnetic particles of the invention may be used for any application of extraction of a material from a liquid. A preferred example is the DNA or RNA extraction, especially from viruses. Advantageously, the use of the particles for the extraction of RNA enables that the number of cycles needed to obtain a signal by the RT-q-PCR method is lowered compared to commercial magnetic particles. There is thus an increase in the sensitivity of the method through the use of the particles obtained by the method of the invention. The cycle number at which the sample becomes detectable by the RT-q-PCR method is referred to as the CT value. The particles obtained by the method of the invention have a lower CT value than commercially available particles. The particles have a CT value of preferably lower than 30.

Herein, the invention is described with reference to specific examples of embodiments of the invention. It will, however, be evident that various modifications, variations, alternatives and changes may be made therein, without departing from the essence of the invention. For the purpose of clarity and a concise description features are described herein as part of the same or separate embodiments, however, alternative embodiments having combinations of all or some of the features described in these separate embodiments are also envisaged and understood to fall within the framework of the invention as outlined by the claims. The specifications, figures and examples are, accordingly, to be regarded in an illustrative sense rather than in a restrictive sense. The invention is intended to embrace all alternatives, modifications and variations which fall within the spirit and scope of the appended claims.

EXAMPLES

Optional Preliminary Step 0

The $Fe_3O_4$ particles used as primary magnetic particles in a dispersion of the process, may be obtained either by a co-precipitation method or by milling.

For the preparation of 4.64 g of $Fe_3O_4$ by co-precipitation method, 5.56 g of iron (II) sulfate heptahydrate and 10.8 g of iron (III) chloride hexahydrate salts are first dissolved in 120 ml of a solution of HCl (0.1M). 200 ml of sodium hydroxide solution (2 molar) was heated at 80° C. under argon flow. Then, iron solution was dropped at 3 ml/minute in the hot sodium hydroxide solution under stirring (at least 400 rpm). After complete addition of iron solution, 20 ml of 28% ammonia solution is added under stirring to the black suspension. The suspension is kept under stirring during 30 min. Heating is then stopped and the suspension remains under stirring until the complete cooling at room temperature. The black precipitate is thoroughly washed with deionized and degassed water until pH reached a value of 7. Then, the black precipitate is washed three times with ethanol before drying the powder.

Figure 1:
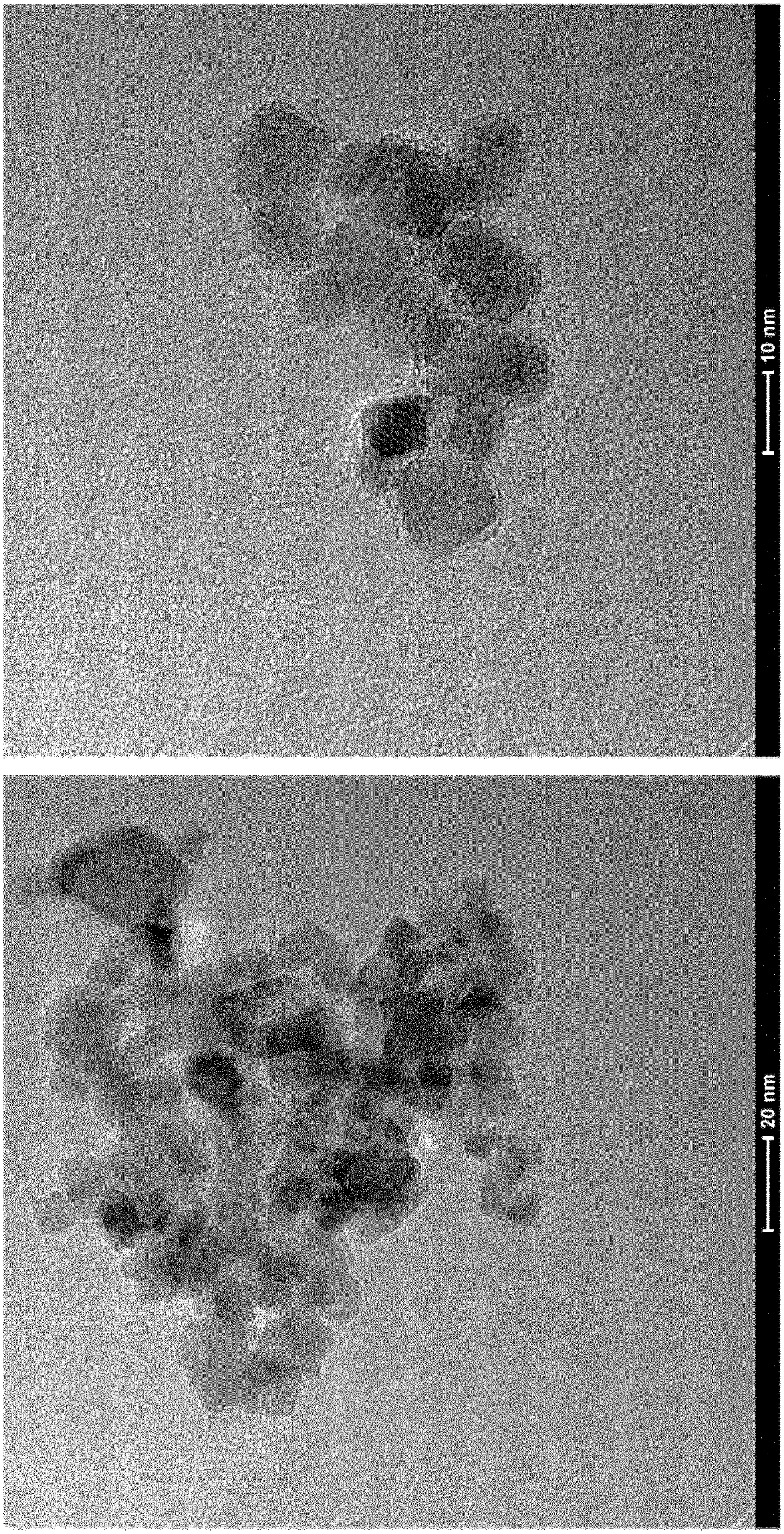
FIG. 1: TEM micrographs of primary $Fe_3O_4$ particles obtained by precipitation route
Figure 2:
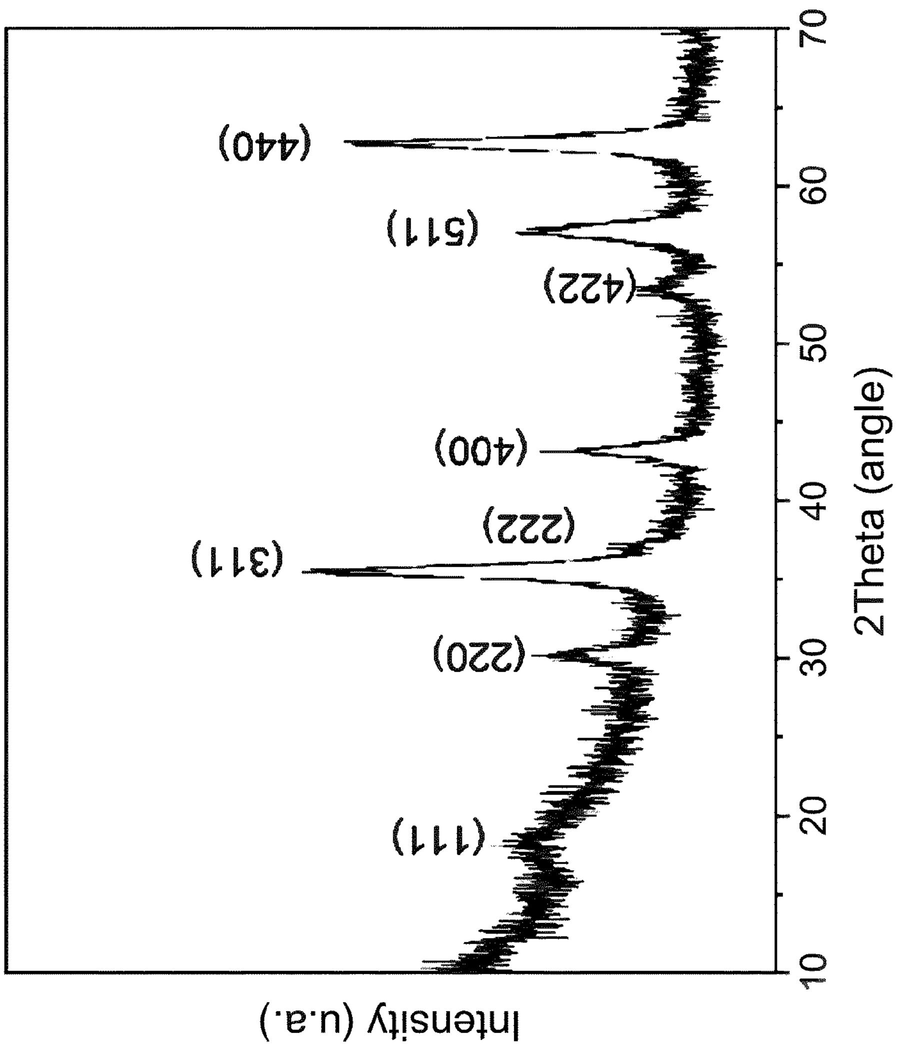
FIG. 2: XRD pattern of primary $Fe_3O_4$ particles obtained by precipitation route

FIG. 1 shows TEM images of $Fe_3O_4$ obtained by the precipitation route. FIG. 2 shows XRD pattern of magnetic $Fe_3O_4$ particles obtained by precipitation. $Fe_3O_4$ primary particles obtained by the precipitation method have an average size of about 15 nm.

For the preparation of $Fe_3O_4$ by milling, a commercial $Fe_3O_4$ powder from ABCR is used. The powder is dispersed in alcohol to obtain a 30 wt % suspension. Then, the suspension is ball-milled with an attritor during between 60 and 120 minutes to reduce the size of the $Fe_3O_4$ particles. It should be understood that the duration of ball-milling may depend on the concentration of particles in the solvent. The duration of ball-milling may be adapted in order to obtain the desired particle size. Preferably the particles are treated under an inert atmosphere to avoid any risk of oxidation. This suspension can be used as feed stock $Fe_3O_4$ suspension for preparing the core-shell particles in the next step or dried to recover $Fe_3O_4$ particles.

Figure 3:
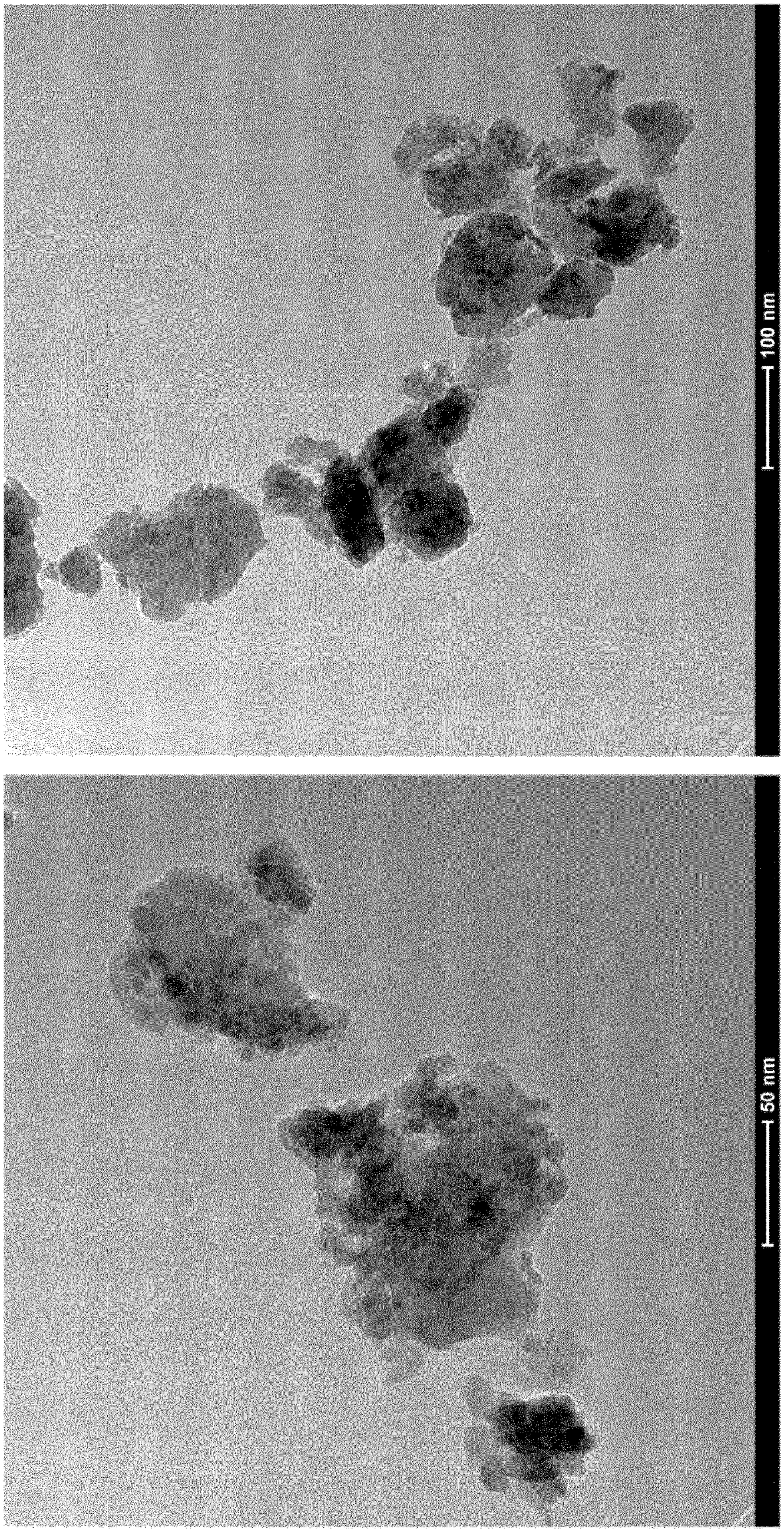
FIG. 3: TEM micrographs of primary $Fe_3O_4$ particles obtained by milling route

FIG. 3 shows TEM images of $Fe_3O_4$ obtained by milling route. Such particles after ball-milling have an average size of about 60 nm.

Figure 3B:
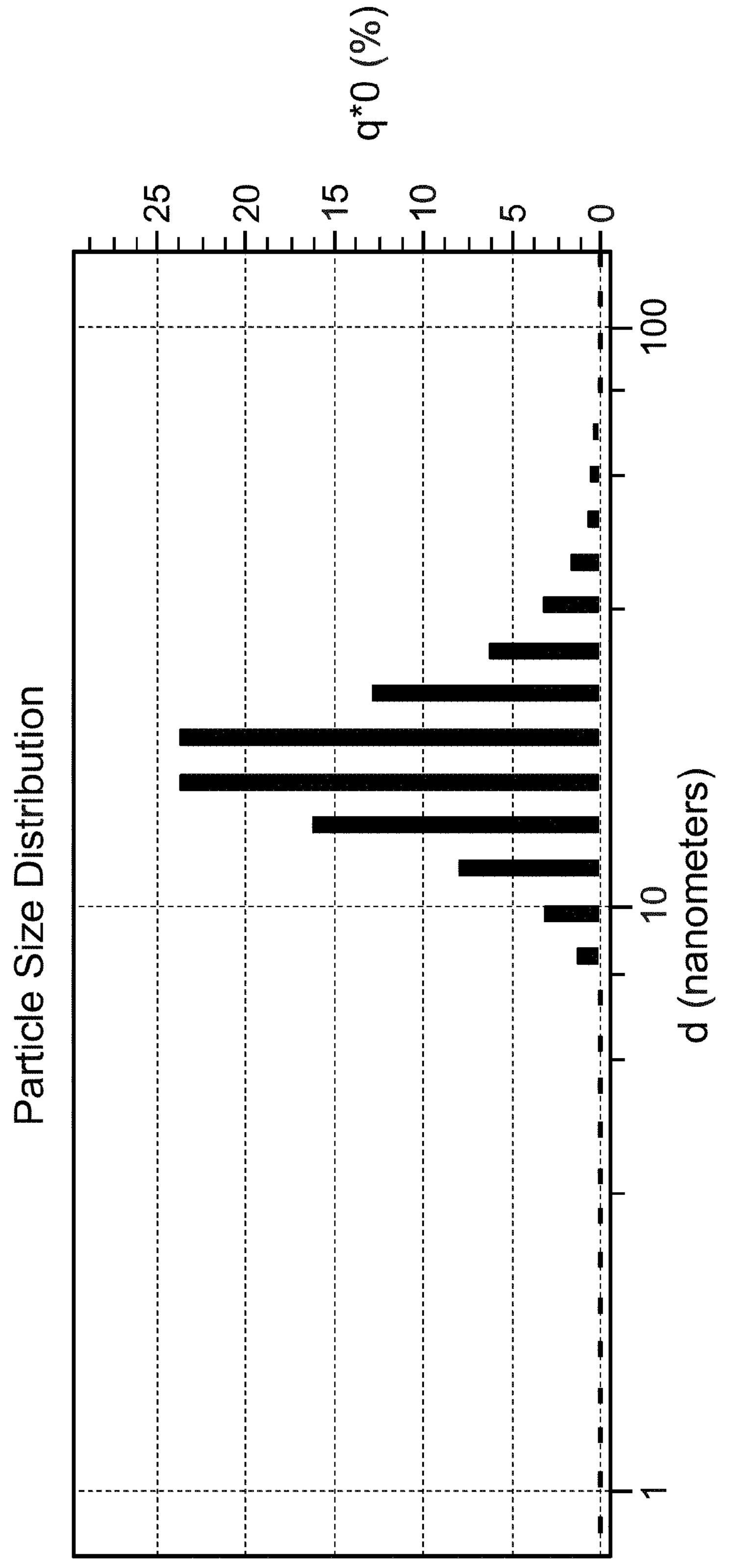
FIG. 3B: Particle size distribution of primary $Fe_3O_4$ obtained by milling route measured by DLS

FIG. 3B shows the particle size distribution of $Fe_3O_4$ after ball-milling.

Example 1

For the preparation of the core-shell particles, 5 g of $Fe_3O_4$ powder obtained by ball-milling (mean diameter of $Fe_3O_4$ primary particles was of 60 nm) were dispersed in 250 ml of pure isopropanol (99.5%). The suspension was treated by ultrasonic probe to enhance the dispersion. Under stirring, 23.7 g of tetraethyl orthosilicate (TEOS) is added to the $Fe_3O_4$ suspension and the weight ratio $SiO_2$:$Fe_3O_4$ in this formulation is of 1.366. 25 ml of concentrated ammonia solution (28 to 30 wt %) was added to 225 ml of milliQ water under stirring. The solution with ammonia is then added in one time to the suspension containing the $Fe_3O_4$ and the TEOS and directly (max 30 seconds) injected by a two-fluid nozzle into a spray-dryer (GEA NIRO-Mobile Minor) under 1 bar pressure. Inlet temperature is fixed at 130° C. and outlet at 80° C. A powder is recovered in the cyclone by adding a magnet inside or outside the bowl.

Figure 4:
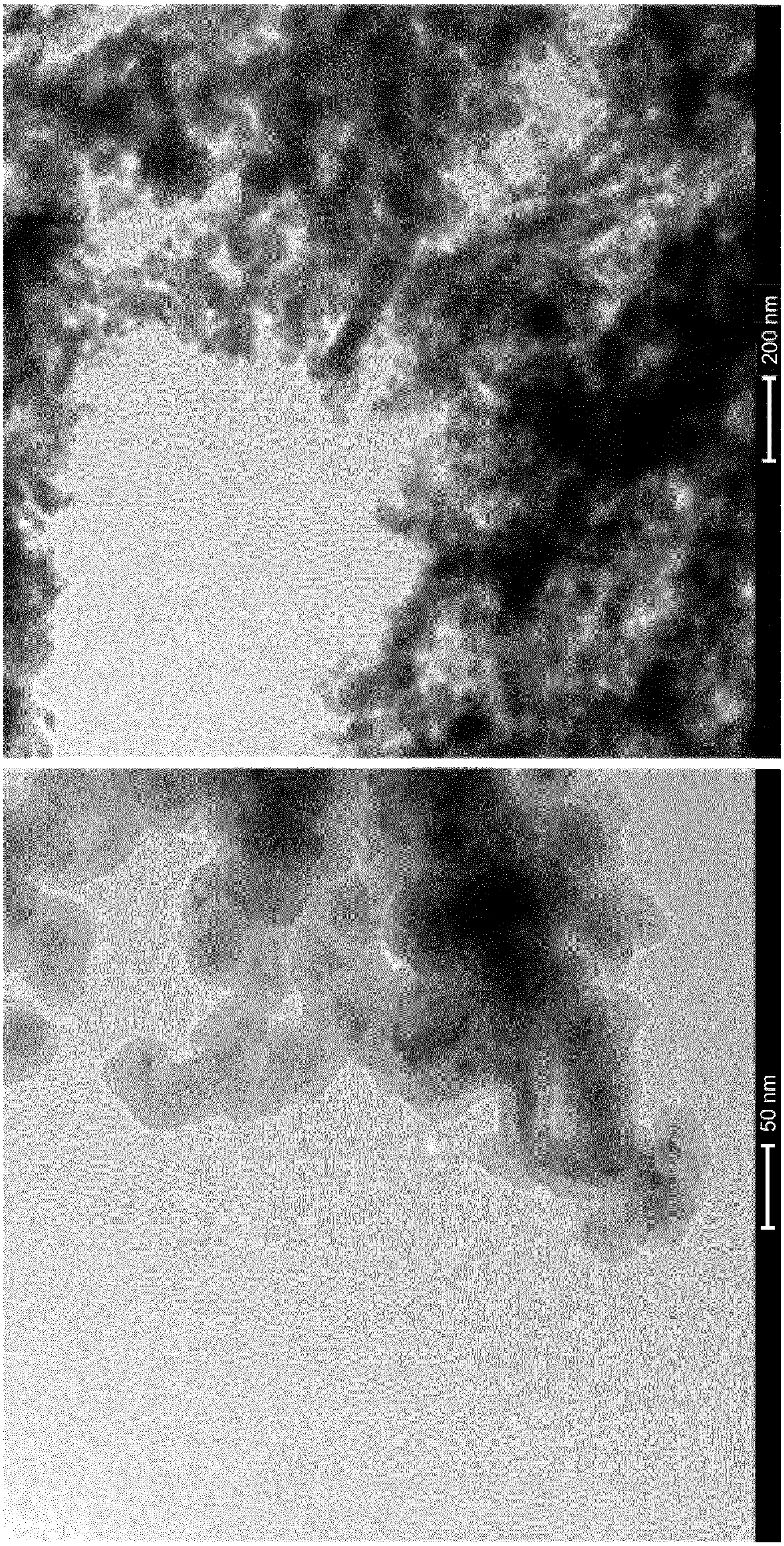
FIG. 4: TEM micrographs of $SiO_2$-coated $Fe_3O_4$ particles obtained in example 1

The process allows to recover about 9.89 g of core-shell particles, with a yield of about 83%. FIG. 4 shows TEM pictures of the powder recovered. We can observe that the particles are formed of a dark heart of $Fe_3O_4$ and a shell of $SiO_2$ having a lighter color. These core-shell particles have an average size of 50 nm. The thickness of the light color shell is about 20 nm. Even, if individual nano-core-shell particles can be clearly observed, we can observe that these nano-core-shell particles are linked together which allows to facilitate the recovery of the powder at the end of the process.

Figure 5:
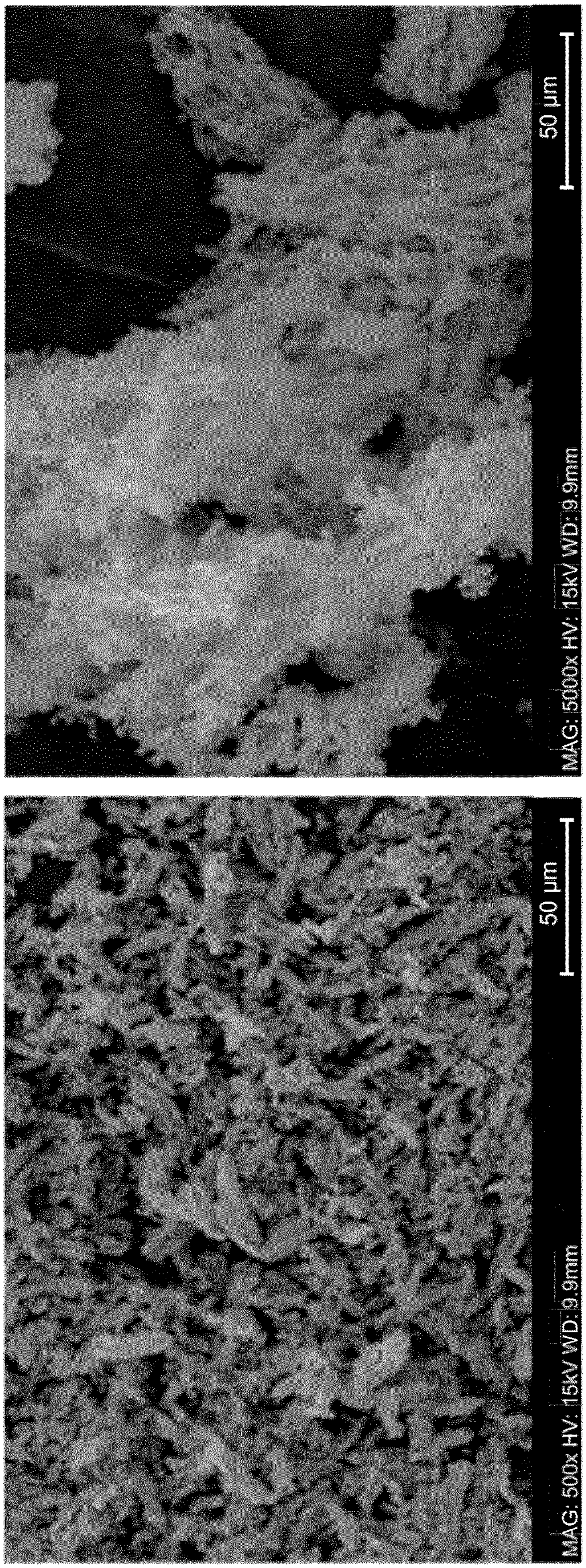
FIG. 5: SEM micrographs of $SiO_2$-coated $Fe_3O_4$ particles obtained in example 1

FIG. 5 shows SEM micrographs of the core-shell particles. Based on FIG. 5, particles have an average size between 10 and 30 μm. These particles are characterized by a spongeous morphology. They are formed by the connection of nano-core-shell particles. This morphology is surprising for a spray drying process. In other processes using spray drying, spherical particles are obtained. Here, the morphology presents a very high porosity, with open pores. An open structure has a beneficial effect with regards to the contact with liquid. These open pores will enable the entry of liquid during the extraction. This morphology is thus particularly efficient for the application of extraction processes. The powder is characterized by a very low bulk density of 0.07 g/ml.

Figure 6:
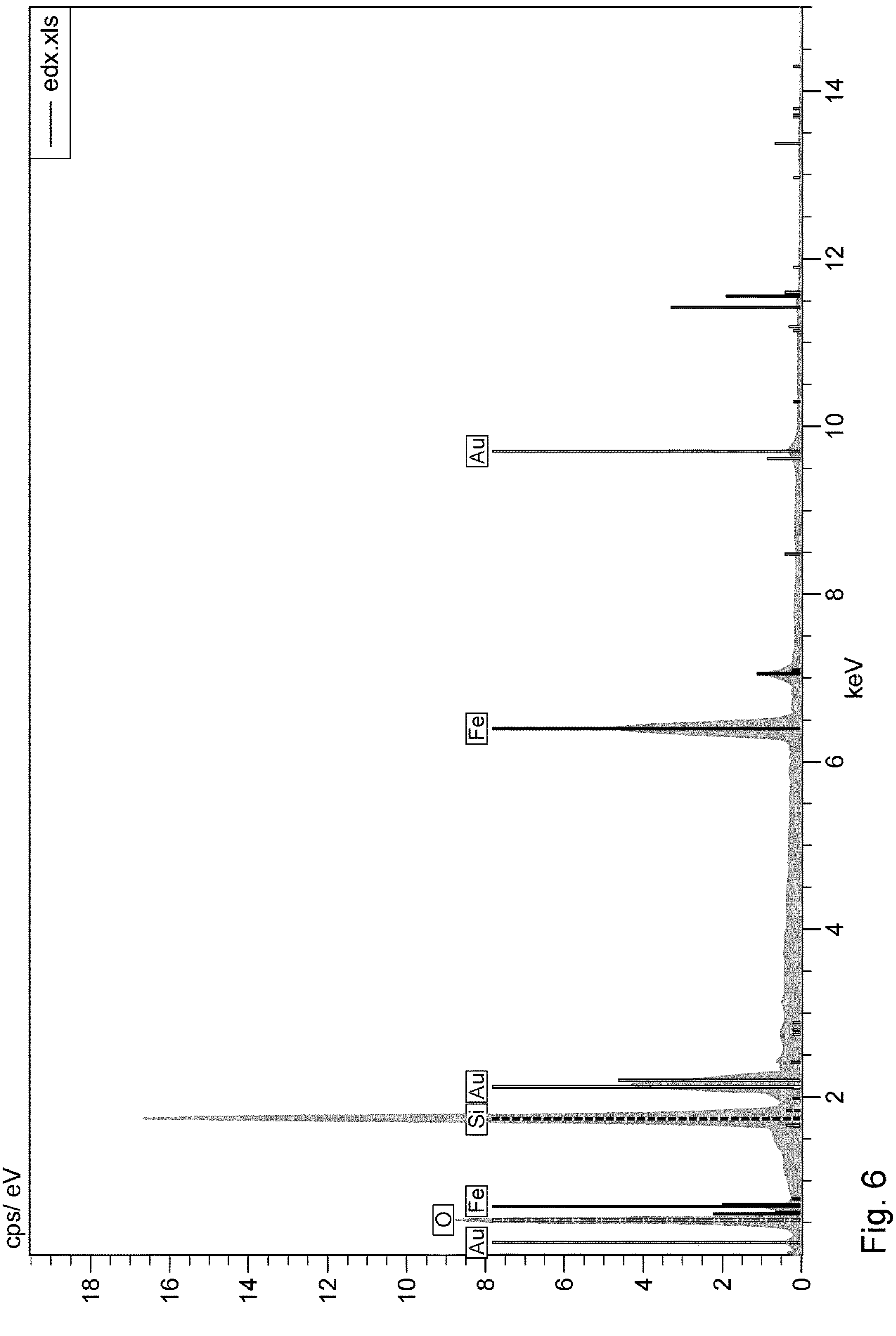
FIG. 6: Energy dispersive X-ray spectrum on $SiO_2$-coated $Fe_3O_4$ particles obtained in example 1

FIG. 6 shows the energy dispersive X-ray spectrum (EDX analysis) performed on the obtained powder. This spectrum confirms the presence of iron and silicon in the powder. Here below is presented the table associated to EDX analysis with different ratio of element present in the powder (gold is due to sample preparation). The table clearly shows that atomic percentage of silicon and iron element are respectively about 28.28 and 24.69.

TABLE 1

EDX analysis of core-shell partides obtained in example 1

| Element | AN | Series | unn. C wt % | norm. C wt % | atom C (at %) | Error (1 sigma) wt % |
|---|---|---|---|---|---|---|
| o | 8 | K-series | 16.99 | 19.88 | 43.74 | 2.26 |
| Si | 14 | K-series | 19.28 | 22.56 | 28.78 | 0.83 |
| Fe | 26 | K-series | 33.46 | 39.16 | 24.69 | 1.03 |
| Au | 79 | M-series | 15.73 | 18.41 | 3.29 | 0.63 |
| | | Total: | 85.46 | 100.00 | 100.0 | |

Figure 7:
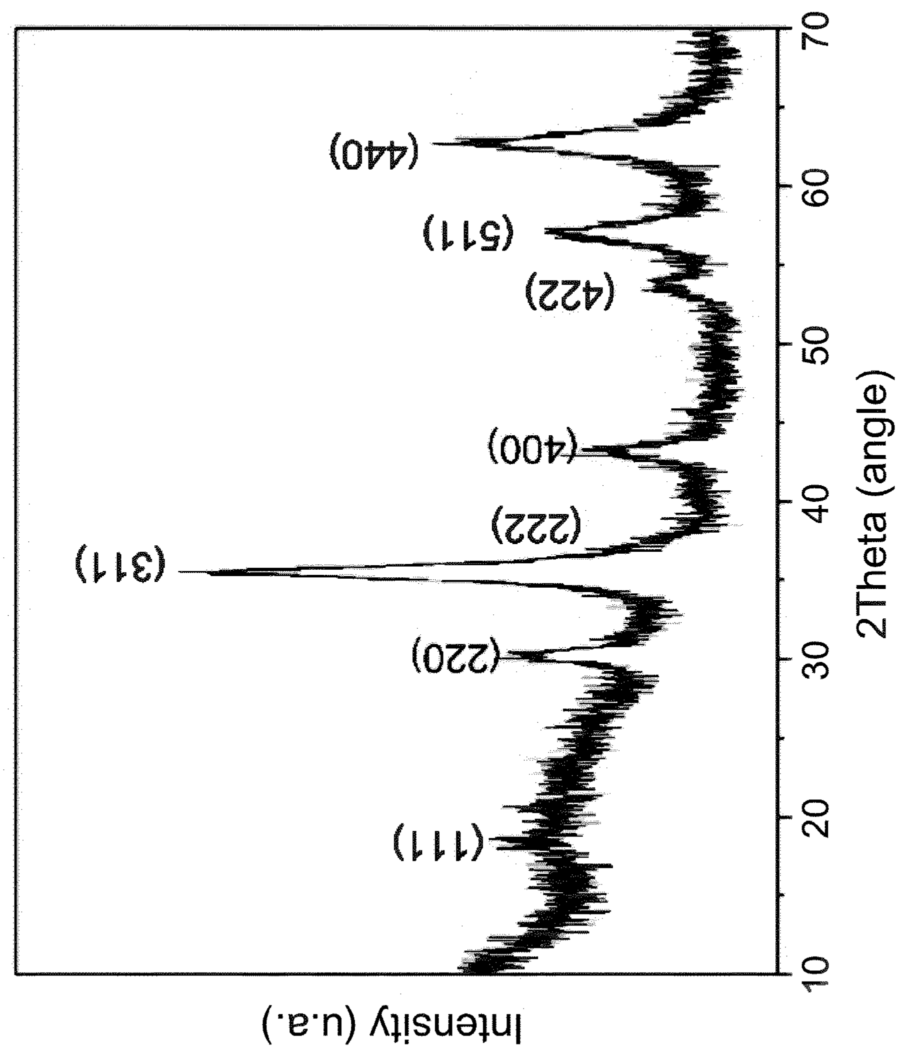
FIG. 7: XRD pattern of $SiO_2$-coated $Fe_3O_4$ particles obtained in example 1

FIG. 7 shows the XRD pattern of the particles. We can clearly observe the peaks attributed to $Fe_3O_4$ phase (compare with FIG. 2) which proves that the drying process does not modify the nature of the $Fe_3O_4$ even if the drying is performed under air in presence of oxygen. Encapsulation of $Fe_3O_4$ by silica coating prevents any oxidation and maintains the magnetic properties of $Fe_3O_4$. Only a broad peak around 25° 2θ can be attributed to the presence of amorphous silica.

Figure 8:
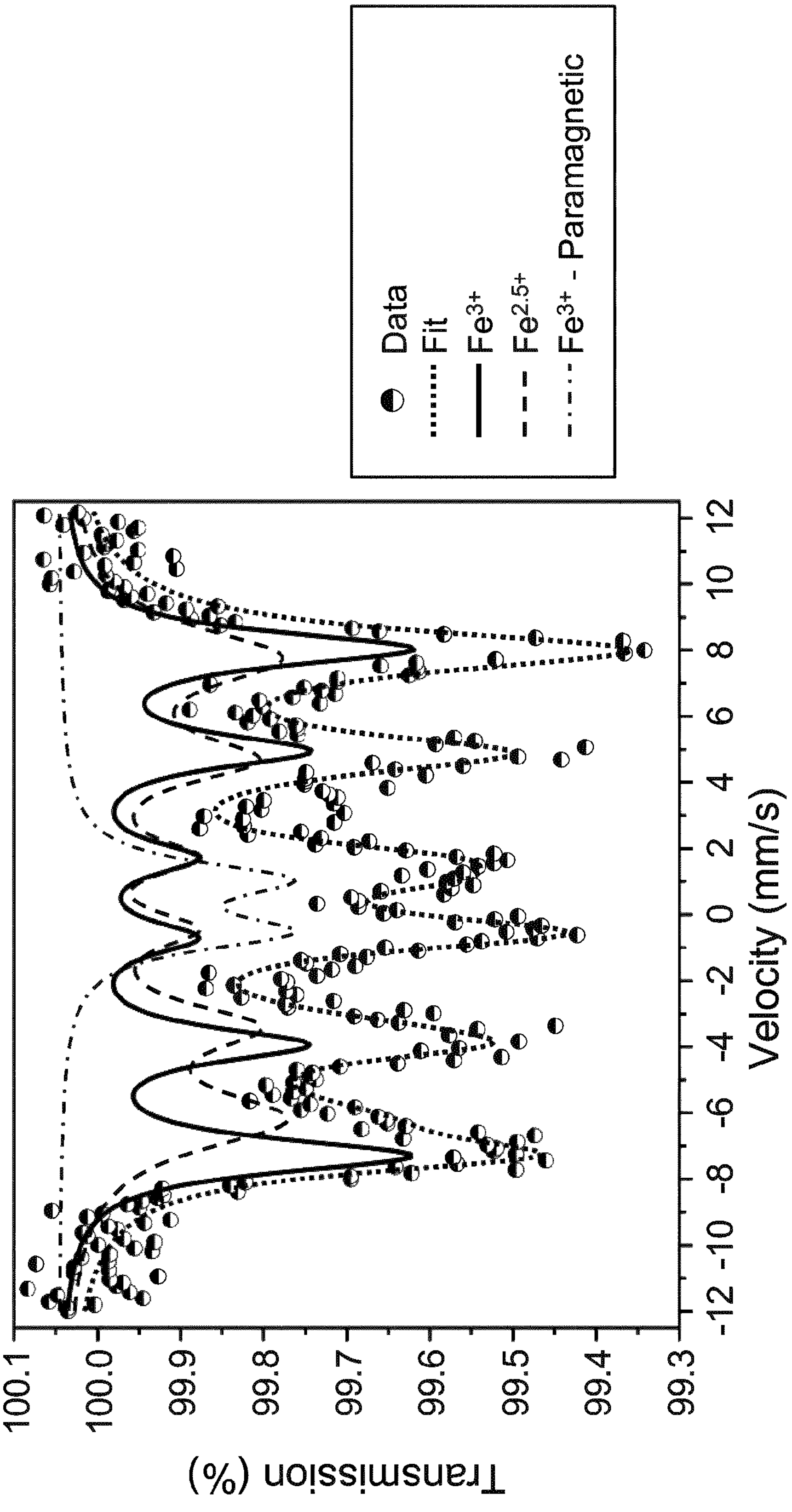
FIG. 8: Mossbauer spectrum recorded at room temperature of $SiO_2$-coated $Fe_3O_4$ particles obtained in example 1

Mössbauer spectroscopy is an excellent technique for probing the oxidation states and the local environment of Fe atoms in oxide materials. The room temperature 57-Fe Mössbauer spectrum of magnetic particles prepared by spray drying method is presented in FIG. 8. Its corresponding Mossbauer parameters are shown in Table 2 below. The Mossbauer spectra at 295 K exhibit well resolved magnetically split sextets, with asymmetric lines indicating different coordination environments for the $Fe^{3+}$ and $Fe^{2.5+}$ ions which are characteristics of $Fe_3O_4$. The doublet is related to paramagnetic phase detected at room temperature. The spectrum shows the presence of two distinct six lines hyperfine patterns, indicating two different types of ferromagnetic Fe atoms in the $Fe_3O_4$ structure which is consistent with the reported Mossbauer results in the literature. Indeed, good quality fit of the Mossbauer spectrum of $Fe_3O_4$ was obtained by using two sextets attributed to $Fe^{3+}$ and $Fe^{2.5+}$ components and one paramagnetic doublet. These sextet subspectra are assigned to iron ions located in A and B positions that present different quadrupole splitting which confirm different local environment of Fe ion in $Fe_3O_4$. The obtained values of the isomer shift and hyperfine fields are consistent with the high spin state of $Fe^{3+}$ and $Fe^{2.5+}$ ions in $Fe_3O_4$. The linewidth of Fe for two sites are relatively high which is related to nanosized particles of the material.

TABLE 2

Mössbauer parameters for core-shell particles obtained in example 1 (δ is Isomer shift, referred to α-iron at 295 K, $\Delta E_Q$ quadrupole splitting, Γ-line width, $H_{hf}$ hyperfine field)

| | |
|---|---|
| $Fe^{3+}$ Magnetic | 43 at % |
| δ (mm $s^{-1}$) | 0.42 |
| $\Delta E_Q$ (mm $s^{-1}$) | −0.13 |
| $H_{hf}$ (T) | 47.6 |
| Γ (mm $s^{-1}$) | 1.13 |
| $Fe^{2.5+}$ Magnetic | 44 at % |
| δ (mm $s^{-1}$) | 0.7 mm/s |
| $\Delta E_Q$ (mm $s^{-1}$) | 0.14 mm/s |
| $H_{hf}$ (T) | 43.7 |
| Γ (mm $s^{-1}$) | 1.17 |
| $Fe^{3+}$ Paramagnetic | 13 at % |
| δ (mm $s^{-1}$) | 0.24 mm/s |
| $\Delta E_Q$ (mm $s^{-1}$) | 1.6 mm/s |
| Γ (mm $s^{-1}$) | 1.29 |

Figure 9:
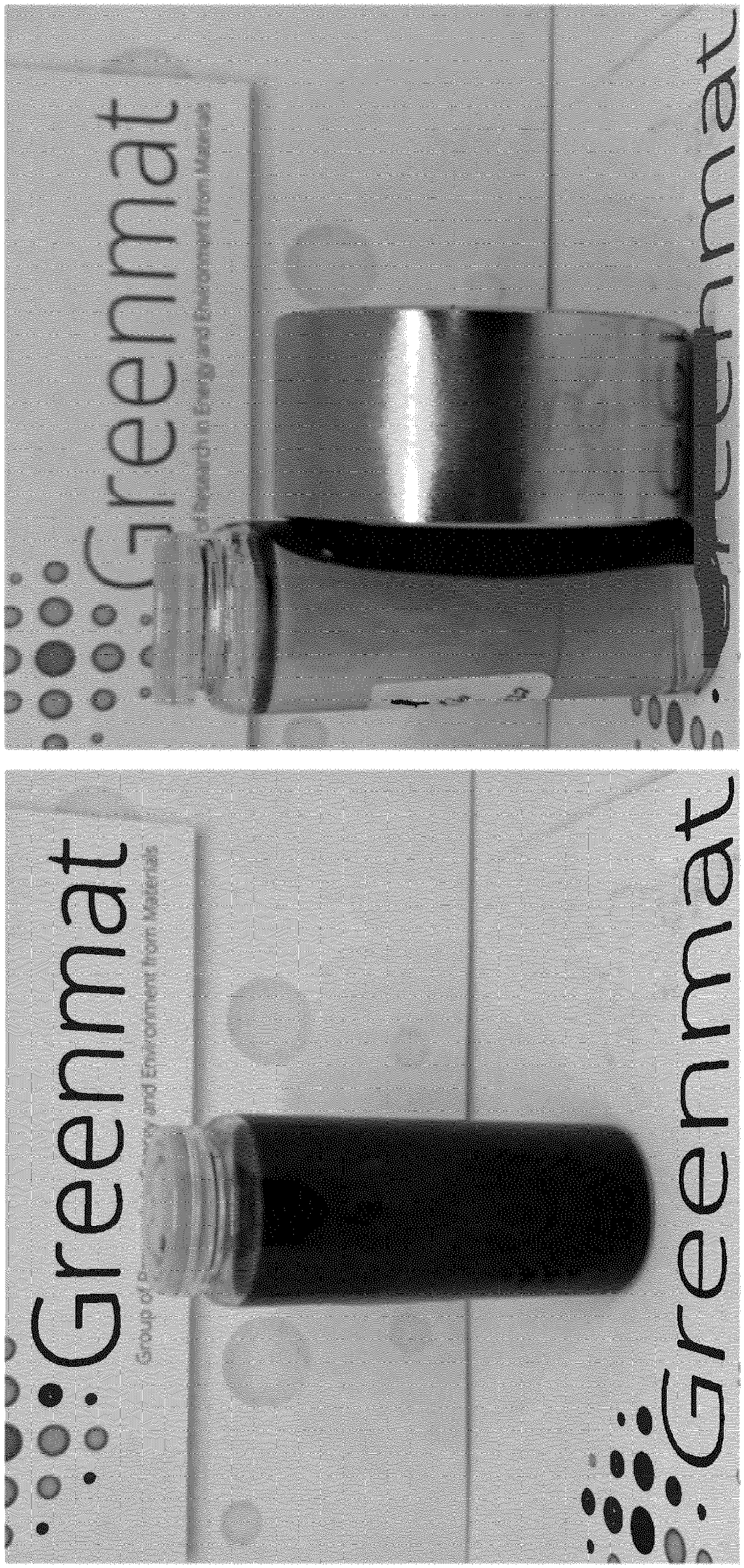
FIG. 9: 1 wt % formulation of $SiO_2$-coated $Fe_3O_4$ particles obtained in example 1, as a dispersion (left), under a magnetic field (right)

FIG. 9 shows the photography of 1 wt % core-shell particles aqueous suspension (left) and the photography of 1 wt % core-shell particles aqueous suspension under a magnetic field (right). It indicates that the particles are characterized by good magnetic properties.

Example 2

Another example of preparing core-shell magnetic particles consists in using colloidal silica suspension as silica precursor. In this example, 5 g of $Fe_3O_4$ powder obtained by ball-milling were dispersed in 455 ml of milliQ water under stirring. The suspension was treated by ultrasonic probe to enhance the dispersion. Under stirring, 25 g of colloidal silica suspension (Ludox HS 40) is added to aqueous suspension of $Fe_3O_4$ particles. The weight ratio $SiO_2$:$Fe_3O_4$ is 2:1. The solution is then directly injected by a two fluid nozzle into a spray-dryer (GEA NIRO-Mobile Minor) under 1 bar pressure. Inlet temperature is fixed at 240° C. and outlet at 125° C. Powder is recovered in the cyclone by adding inside of the bowl a magnet.

Figure 10:
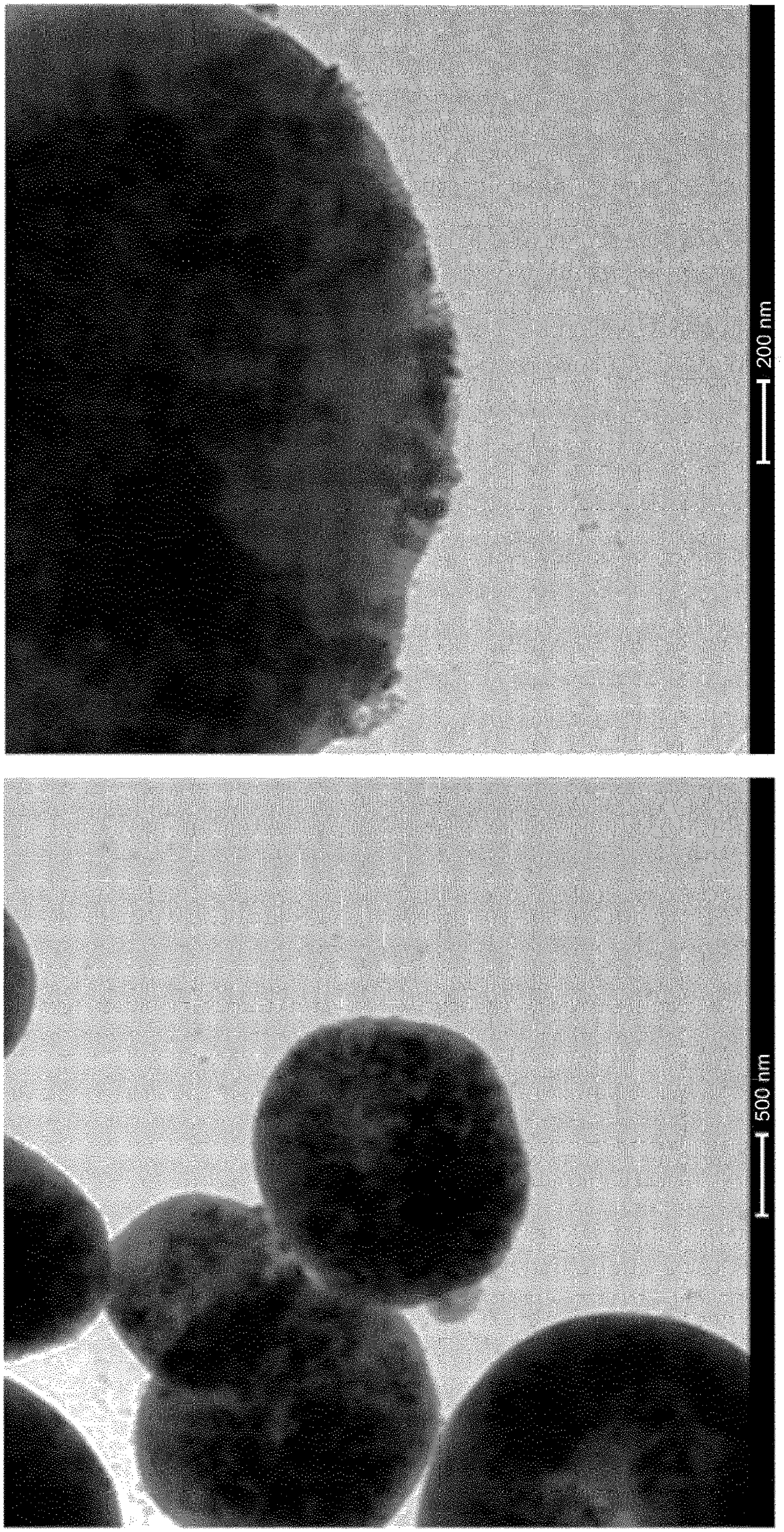
FIG. 10: TEM micrographs of $SiO_2$-coated $Fe_3O_4$ particles obtained in example 2
Figure 11:
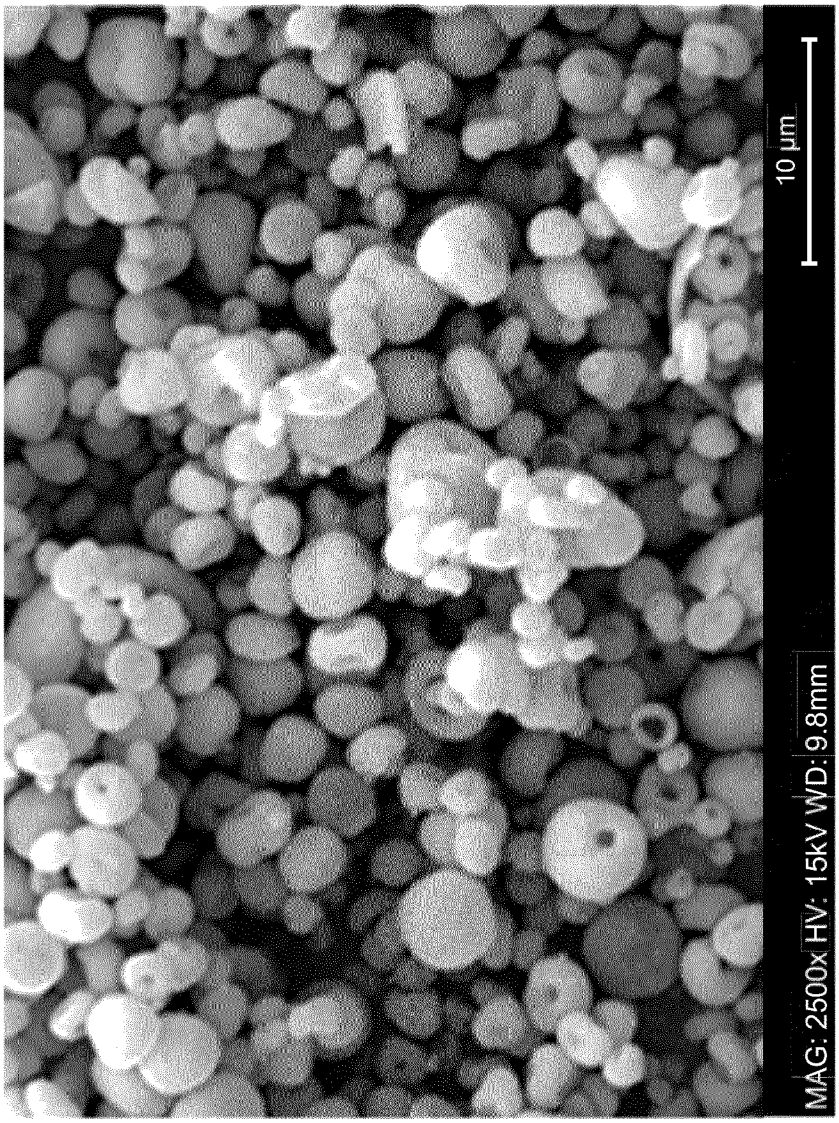
FIG. 11: SEM micrographs of $SiO_2$-coated $Fe_3O_4$ particles obtained in example 2
Figure 12:
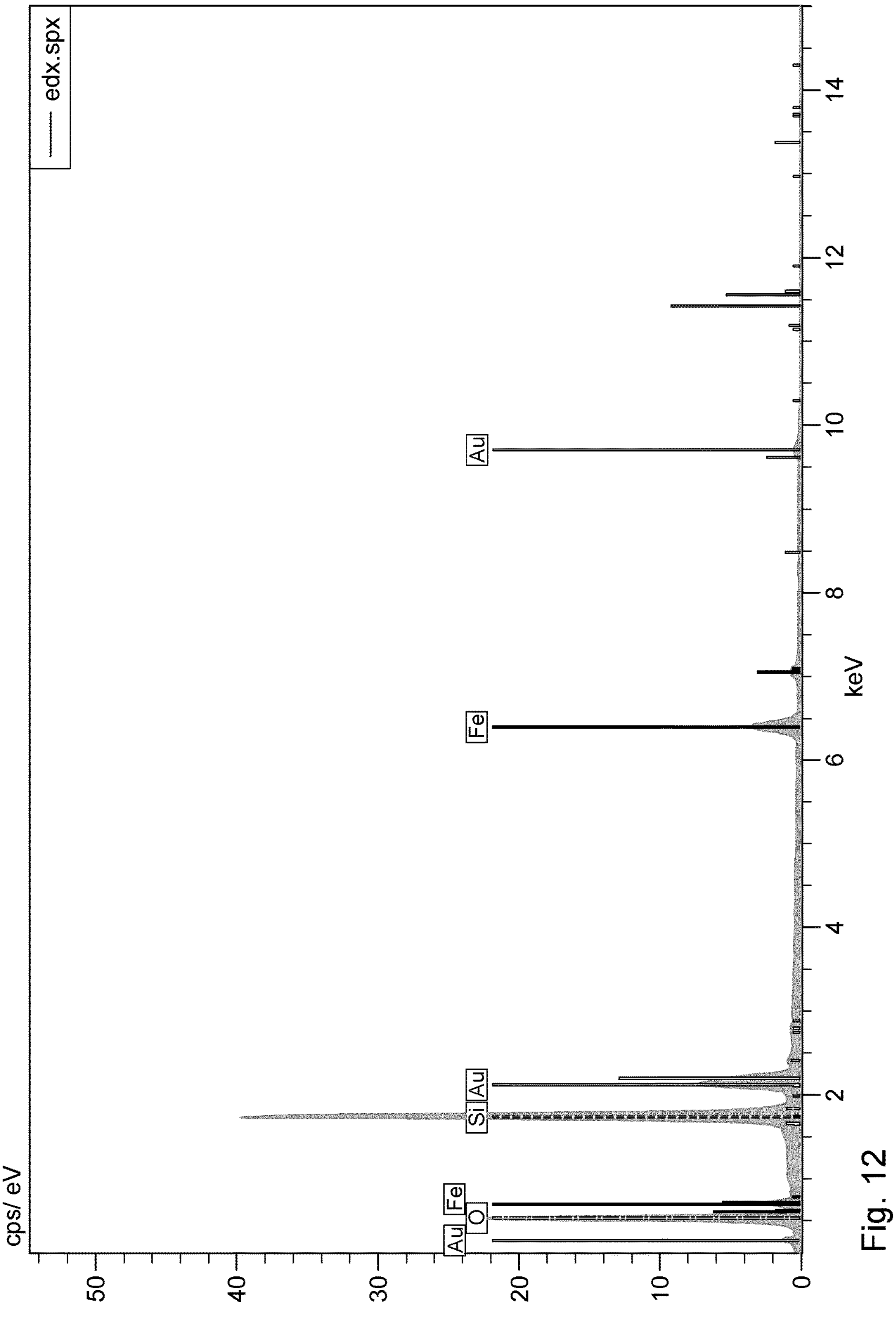
FIG. 12: Energy dispersive X-ray spectrum on $SiO_2$-coated $Fe_3O_4$ particles obtained in example 2

The process allows to recover about 7.1 g of particles, which corresponds to a yield of about 46.3%. FIG. 10 shows TEM pictures of the powder recovered. We can observe that micronic particles are formed by this method. They are formed by a dark grey heart of $Fe_3O_4$ and encapsulated in a light grey color matrix of $SiO_2$. We can observe small primary colloidal silica particles onto the surface of the micronic core-shell particles. FIG. 11 shows SEM micrographs of the obtained particles. Based on FIG. 11, particle size has an average size between 2 and 6 μm. These particles are characterized by a pseudospherical morphology and a smooth surface and a bulk density of 0.41 g/ml. FIG. 12 shows the energy dispersive X-ray spectrum (EDX analysis) performed on this sample. This spectrum confirms the presence of iron and silicon in the powder. The table below is associated to EDX analysis with different ratio of element present in the powder (gold is due to sample preparation). The table shows that atomic percentage of silicon and iron element are respectively about 22.8 and 18.16.

TABLE 3

EDX analysis of core-shell particles obtained in example 2

| Element | AN | Series | wt % | norm. wt % | norm. at. %) | Error (1 sigma) wt % |
|---|---|---|---|---|---|---|
| O | 8 | K-series | 26.49 | 31.93 | 57.65 | 3.08 |
| Si | 14 | K-series | 22.82 | 27.51 | 28.29 | 0.97 |
| Fe | 26 | K-series | 18.17 | 21.90 | 11.33 | 0.57 |
| Au | 79 | M-series | 15.47 | 18.66 | 2.74 | 0.61 |
| | | Total: | 82.95 | 100.00 | 100.0 | |

Figure 13:
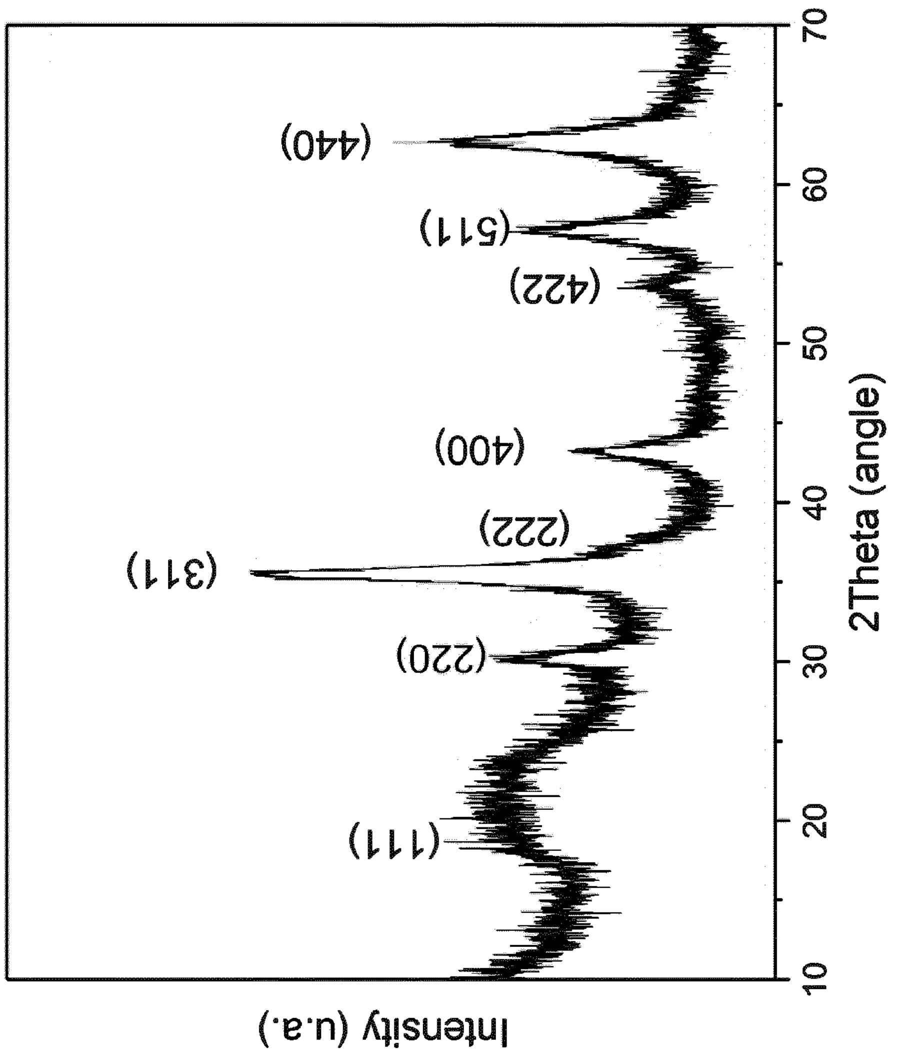
FIG. 13: XRD pattern of $SiO_2$-coated $Fe_3O_4$ particles obtained in example 2
Figure 14:
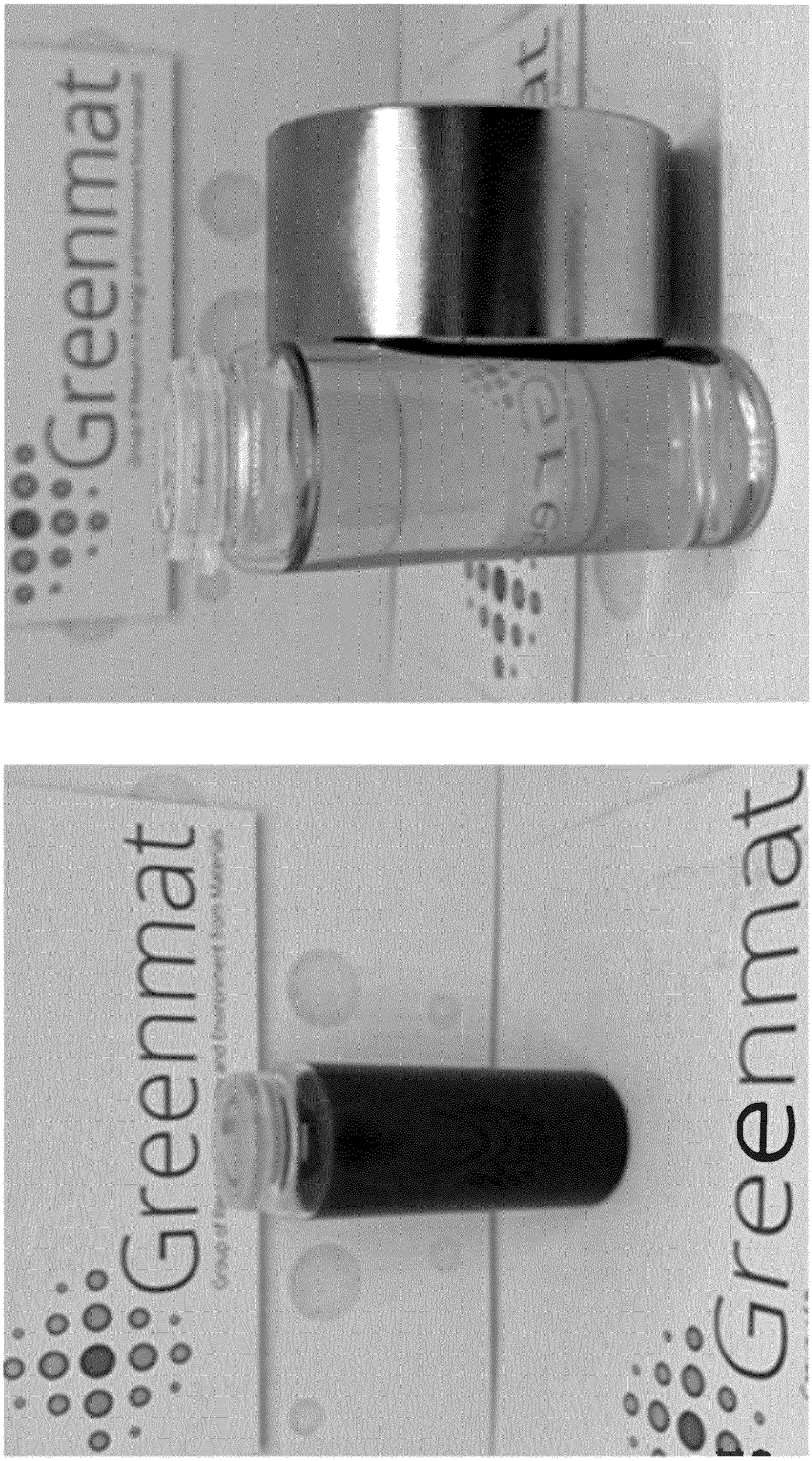
FIG. 14: 1 wt % formulation of $SiO_2$-coated $Fe_3O_4$ particles obtained in example 2, as a dispersion (left), under a magnetic field (right)

FIG. 13 shows XRD pattern of the obtained particles. We can observe the peaks attributed to $Fe_3O_4$ phase (compared with those of FIG. 2) which proves that drying process does not modify the nature of $Fe_3O_4$. Encapsulation of $Fe_3O_4$ by silica coating prevents any oxidation and guarantees the magnetic properties of $Fe_3O_4$. Only a broad peak around between 20 and 25° 2θ can be attributed to the presence of amorphous silica. FIG. 14 shows the photography of 1 wt % aqueous suspension of particles obtained in example 2 (left) and the photography of 1 wt % aqueous suspension of particles obtained in example 2 under a magnetic field (right) which confirms that the particles are characterized by good magnetic properties. RNA extraction of Pneumovirus of mice has been performed with those particles under the same protocol as example 1. Particles are characterized by a CT value of 25.0.

Example 3

As a further example, the conditions of outlet temperature, flow rate and injection pressure were varied. Core-shell particles were prepared in a similar manner as in example 1.

5 g of $Fe_3O_4$ powder obtained by ball-milling were dispersed in 230 ml of pure isopropanol (99.5%). Suspension was treated by ultrasonic probe to enhance the dispersion. Under stirring, 23.7 g of tetraethyl orthosilicate (TEOS) is added to the $Fe_3O_4$ suspension and weight ratio TEOS/$Fe_3O_4$ in this formulation is of 1.366. 25 ml of concentrated ammonia solution (28 to 30% mass) was added to 225 ml of milliQ water under stirring. The solution with ammonia is then added in one time to the suspension containing the $Fe_3O_4$ and the TEOS and directly injected by a two-fluid nozzle into a spray-dryer (GEA NIRO-Mobile Minor). Injection pressure is varied between 1 and 3 bar, outlet temperature between 60 and 100° C. and flow rate between 25 and 50 ml/minute to evaluate the robustness of the process. Powder is recovered in the cyclone by adding a magnet inside the bowl.

Figure 15:
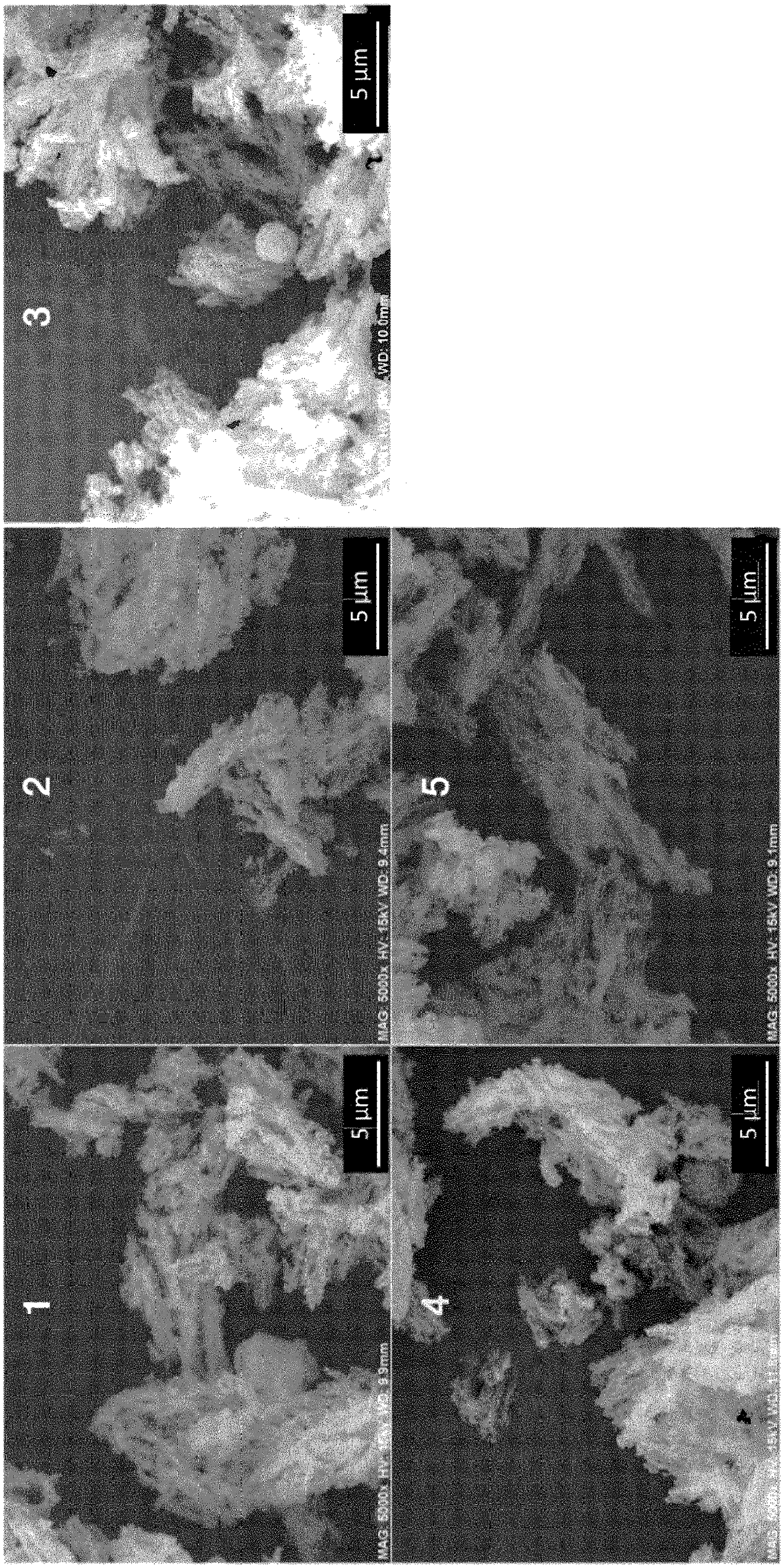
FIG. 15: SEM micrographs of core-shell particles obtained at different outlet temperature (1,2,3), at different flow rate (1,4) and at different injection pressure (1,5).

Table 4 summarizes the evolution of granulometric factors, bulk density, yield and specific surface area according to the parameters (outlet temperature increasing and decreasing, flow rate and injection pressure). FIG. 15 shows SEM micrographs of the obtained core-shell particles. All have a spongeous morphology with a Si:Fe atomic ratio of 1:1. Modification of outlet temperature (±20° C.) has no effect on the microstructure of the particle. No significant change can be observed concerning size, yield and specific surface area.

Increase of flow rate and injection pressure does not significantly modify particle size, density, yield and BET specific surface area. The obtained particles present a similar morphology, showing the robustness of the process. All particles obtained are core-shell particles. Hence, this process is highly versatile.

TABLE 4

Granulometric parameters, bulk density, yield and BET specific surface area for core-shell powders produced using different experimental conditions Effect of outlet temperature

| Number | Temperature (° C.) | D 0.5 (μm) | D 0.9 (μm) | Density (g/mL) | Yield (%) | Specific surfaces area-BET ($m^2$/g) |
|---|---|---|---|---|---|---|
| 1 | 81 | 4.2 | 10.4 | 0.065 | 75.4 | 60.28 |
| 2 | 61 | 3.5 | 7.5 | 0.066 | 77.3 | not available |
| 3 | 101 | 4.1 | 10.4 | 0.066 | 72.4 | 48.71 |

Effect of flow rate (ml/min)

| Number | Flow rate (ml/min) | D 0.5 (μm) | D 0.9 (μm) | Density (g/mL) | Yield (%) | Specific surfaces area-BET ($m^2$/g) |
|---|---|---|---|---|---|---|
| 1 | 25 | 4.2 | 10.4 | 0.065 | 75.4 | 60.28 |
| 4 | 50 | 3.3 | 8.3 | 0.070 | 75.1 | not available |

Effect of injection pressure

| Number | injection pressure (bar) | D 0.5 (μm) | D 0.9 (μm) | Density (g/mL) | Yield (%) | Specific surfaces area-BET ($m^2$/g) |
|---|---|---|---|---|---|---|
| 1 | 1 | 4.2. | 10.4 | 0.065 | 75.4 | 60.28 |
| 5 | 3 | 3.8 | 8.8 | 0.066 | 70.7 | 50.74 |

Example 4

As a further example, ratio of TEOS versus $Fe_3O_4$ was varied. Core-shell particles were prepared in a similar manner as in example 1.

5 g of $Fe_3O_4$ powder obtained by ball-milling was dispersed in 230 ml of pure isopropanol (99.5%). Suspension was treated by ultrasonic probe to enhance the dispersion. Under stirring, 2.37, 11.85, 17.78, 23.7 or 47.4 g of TEOS is added to the $Fe_3O_4$ suspension and weight ratio TEOS/$Fe_3O_4$ in this formulation is respectively of 0.1366, 0.683, 1.025, 1.366, 2.732. 25 ml of concentrated ammonia solution (28 to 30% mass) was added to 225 ml of milliQ water under stirring. The solution with ammonia is then added in one time to the suspension containing the $Fe_3O_4$ and the TEOS and directly injected by a two-fluid nozzle into a spray-dryer (GEA NIRO-Mobile Minor) under 1 bar pressure. Inlet temperature is fixed at 130° C. and outlet at 80° C. Powder is recovered in the cyclone by adding a magnet inside the bowl.

Figure 16:
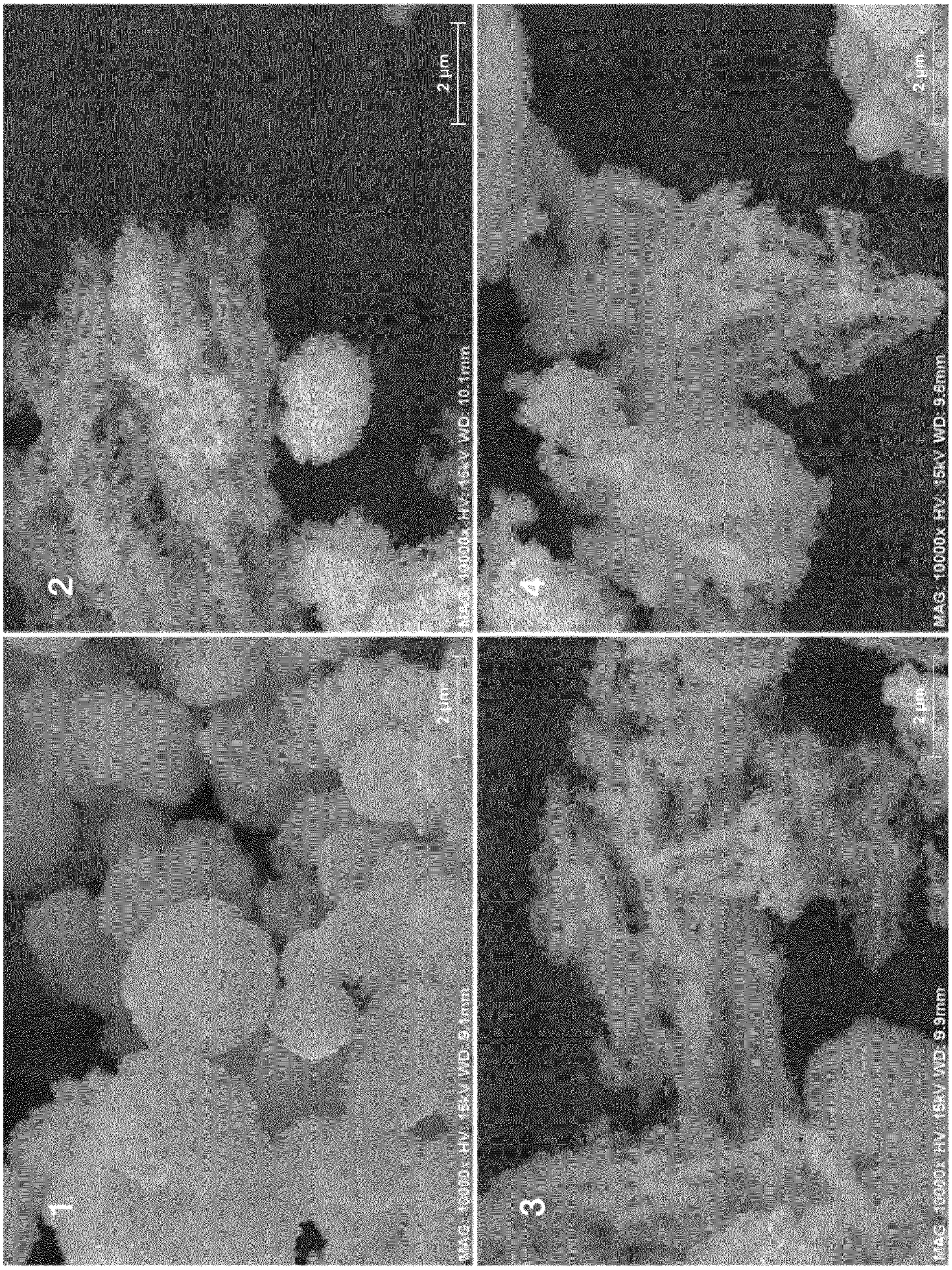
FIG. 16: Scanning electron micrographs of core-shell particles obtained at different mass ratio of TEOS:$Fe_3O_4$ (1) 0.1366:1; (2) 0.683:1; (3) 1.025:1; (4) 1.366:1
Figure 17:
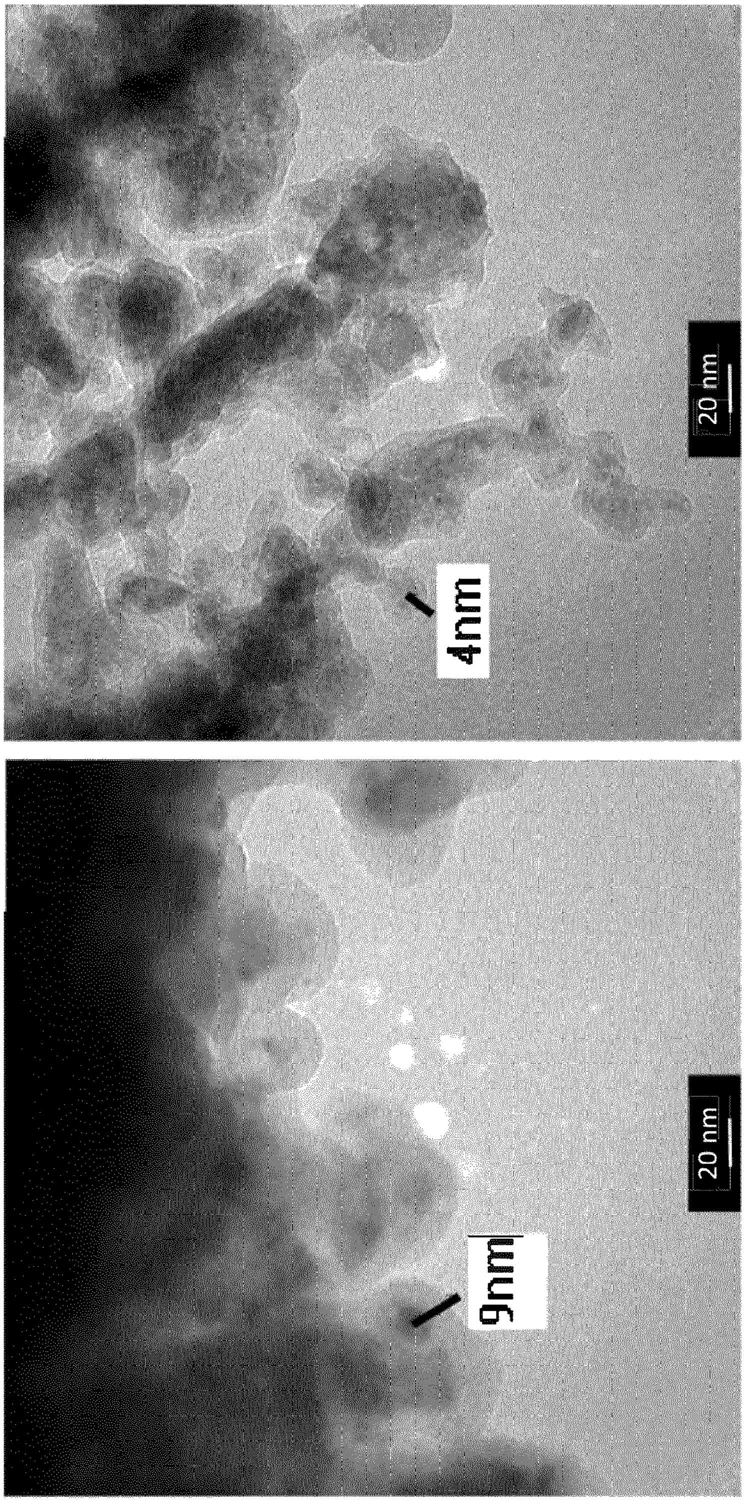
FIG. 17: TEM micrographs of core-shell particles obtained using a TEOS: $Fe_3O_4$ of 2.732:1 (left) and using a TEOS:$Fe_3O_4$ of 0.683:1 (right)
Figure 18:
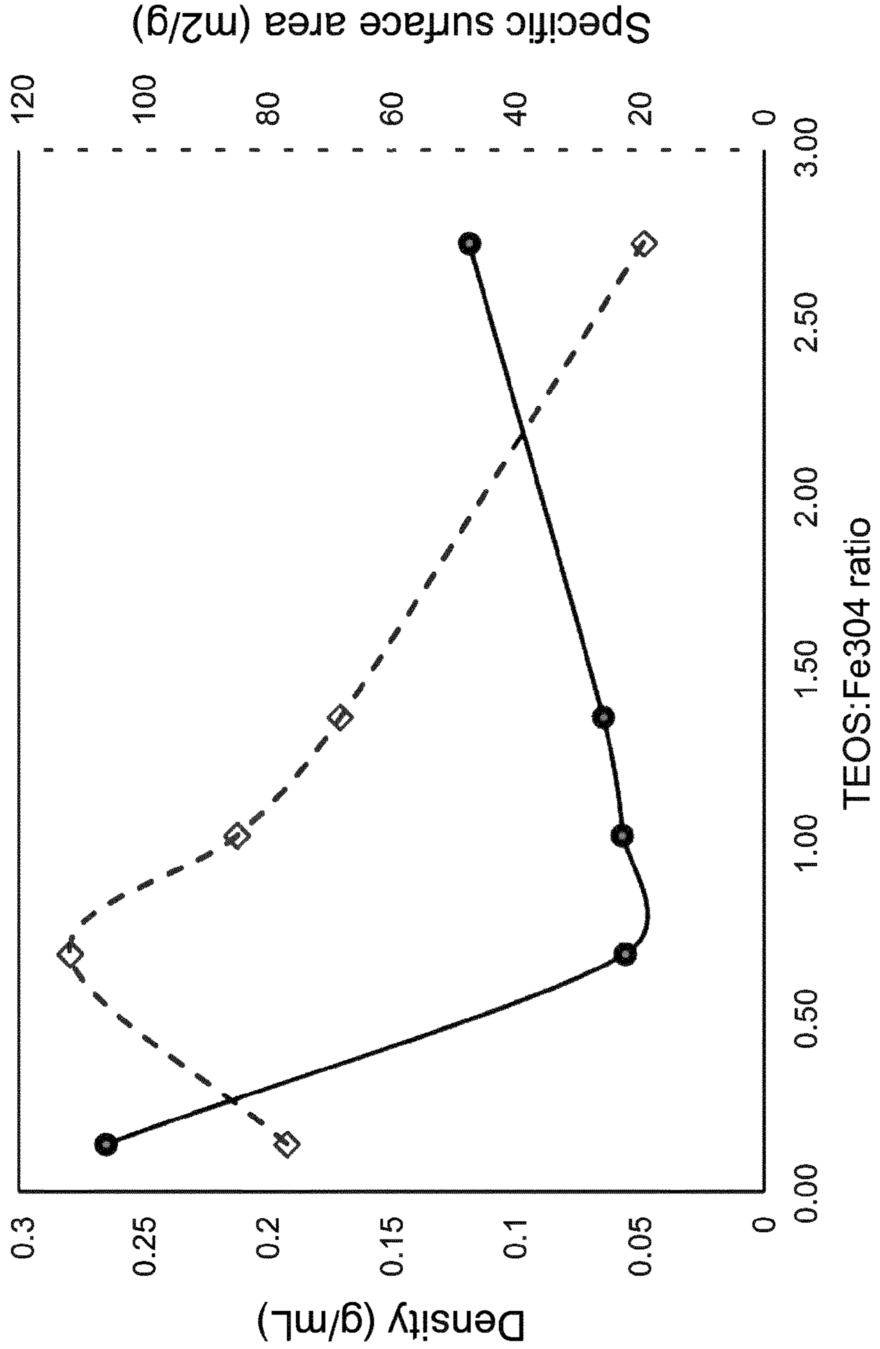
FIG. 18: Evolution of the bulk density (full line) and specific surface area of the powder (dots) as a function of TEOS:$Fe_3O_4$ ratio

Table 5 shows particle size (D.05 and D0.9) and atomic ratio Si/Fe measured by EDX for powder obtained after synthesis following the initial ratio TEOS:$Fe_3O_4$. Increase of the ratio TEOS:$Fe_3O_4$ leads to the increase of particle size from 2.1 to 4.4 m for respectively 0.1366:1 to 2.732:1 TEOS:$Fe_3O_4$ ratio. SEM micrographs (FIG. 16) show a morphological difference between particles according to the TEOS concentration with a more spherical shape at low TEOS:$Fe_3O_4$ ratio of 0.1366:1. Atomic ratio Si:Fe (Table 5) measured by EDX indicates that the increase of TEOS:$Fe_3O_4$ leads to enrichment of core-shell particle in $Fe_3O_4$. This means that the amount of silica shell and thickness of shell can be precisely controlled during the preparation of the solution. TEM micrographs (FIG. 17) clearly shows that thickness of silica shell increases with TEOS:$Fe_3O_4$ ratio (see larger shell on particles obtained using a TEOS:$Fe_3O_4$ of 2.732:1, left picture). Specific surface is a key property for surface exchange reaction and kinetic of exchange, specific surface can be modified according to TEOS:$Fe_3O_4$ ratio as shown in FIG. 18. The highest specific surface was obtained for TEOS:$Fe_3O_4$ ratio 0.683:1 and was 111 $m^2/g$. Moreover, we can observe that an inverse correlation can be established between bulk density of core-shell powder and specific surface area (FIG. 18), with the lowest bulk density of 0.056 g/ml for the powder obtained with TEOS:$Fe_3O_4$ 0.683:1 which fits with the highest specific surface area value. Adjusting TEOS:$Fe_3O_4$ ratio allows to define the physico-chemical properties of the core-shell powder and to adapt those for the desired application.

TABLE 5

Particle size and atomic ratio Si:Fe according to mass ratio of TEOS:$Fe_3O_4$

| Number | Mass ratio of TEOS:$Fe_3O_4$ | D 0.5 (μm) | D 0.9 (μm) | Atomic ratio Si:Fe |
|---|---|---|---|---|
| 1 | 0.1366:1 | 2.1 | 4.3 | 0.14:1 |
| 2 | 0.683:1 | 3.2 | 7.1 | 0.63:1 |
| 3 | 1.025:1 | 3.9 | 9.7 | 0.82:1 |
| 4 | 1.366:1 | 4.2 | 10.4 | 1.16:1 |
| 5 | 2.732:1 | 4.4 | 10.6 | 1.88:1 |

Example 5

To show the versatility of the process, core-shell magnetic particles were prepared using colloidal boehmite suspension, in a similar manner as in example 1.

For the preparation of the core-shell particles, 5 g of $Fe_3O_4$ powder obtained by ball-milling was dispersed in 230 ml of pure isopropanol (99.5%). Suspension was treated by ultrasonic probe to enhance the dispersion. Under stirring, 3.12 g or 6.25 g of boehmite powder (Dequadis) is added to 250 ml of milliQ water to obtain a well dispersed boehmite sol to reach a weight ratio boehmite:$Fe_3O_4$ in the formulation of 0.624 or 1.249. This suspension is added under stirring to $Fe_3O_4$ suspension and directly injected by a two-fluid nozzle into a spray-dryer (GEA NIRO-Mobile Minor) under 1 bar pressure. Inlet temperature is fixed at 130° C. and outlet at 80° C. Powder is recovered in the cyclone by adding a magnet inside the container.

In Table 6, we can observe that particle size and density do not depend on boehmite:$Fe_3O_4$ ratio. Size is around 1.8 m with a very narrow distribution with d(0.9) value around 3.2 m. However, boehmite:$Fe_3O_4$ ratio allows to control the specific surface area and the atomic ratio Al:Fe in the powder. The use of sol boehmite allows to obtain core-shell particles with a high specific surface area with a value of 185 $m^2/g$ for 1.249:1 boehmite:$Fe_3O_4$ ratio with bulk density of 0.42 g/ml. Control of Al:Fe can be easily achieved through boehmite:$Fe_3O_4$ ratio in the suspension before spray-drying.

Figure 19:
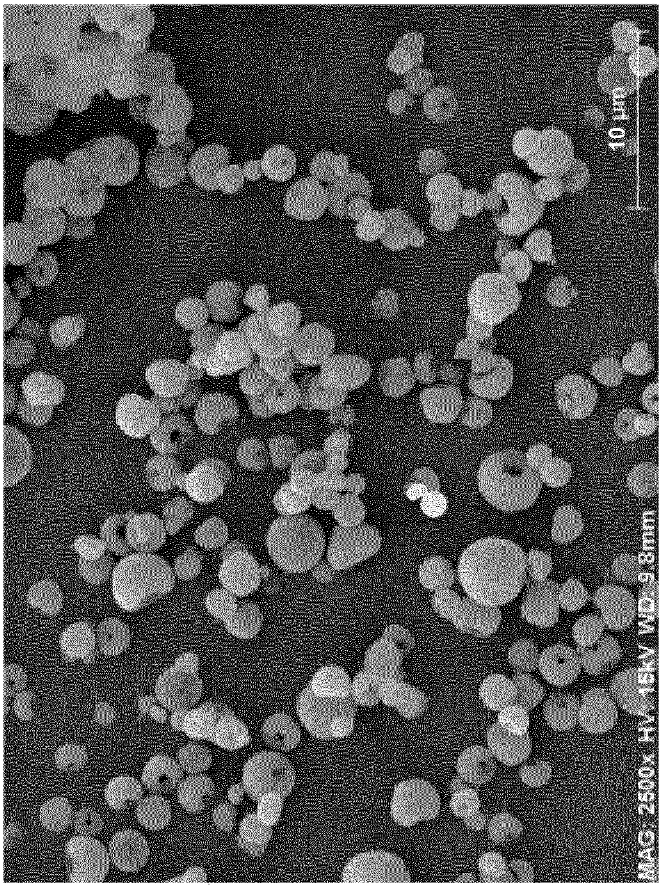
FIG. 19: SEM micrographs of core-shell particles with boehmite, with boehmite:$Fe_3O_4$ ratio of 1.249:1

FIG. 19 shows SEM micrographs of particles obtained after spray-drying. Pseudospherical non agglomerated core-shell boehmite-$Fe_3O_4$ with narrow size distribution and smooth surface were obtained.

TABLE 6 particle size, specific surface area and atomic ratio Al:Fe according to the mass ratio of boehmite:$Fe_3O_4$

| Weight ratio Boehmite:Fe3O4 | D0.5 (μm) | D0.9 (μm) | BET specific surface area (m2/g) | Density (g/mL) | Atomic ratio Al:Fe |
|---|---|---|---|---|---|
| 0.624:1 | 1.8 | 3.2 | 134 | 0.46 | 0.91:1 |
| 1.249:1 | 1.8 | 3.4 | 185 | 0.42 | 1.18:1 |

Example 6

To further show the versatility of the process, core-shell magnetic particles were prepared using titania, in a similar manner as in example 1.

For the preparation of the core-shell $TiO_2$—$Fe_3O_4$ particles, 5 g of $Fe_3O_4$ powder obtained by ball-milling was dispersed in 230 ml of pure isopropanol (99.5%). Suspension was treated by ultrasonic probe to enhance the dispersion. Under stirring, 16.16 g of titanium (IV) tetraisopropoxide is added to 250 ml of pure isopropanol to obtain a solution to reach a weight ratio $TiO_2$:$Fe_3O_4$ in the formulation of 0.682:1. This solution is added under stirring to $Fe_3O_4$ suspension and directly injected through a two-fluid nozzle into a spray-dryer (GEA NIRO-Mobile Minor) under 1 bar pressure. Due to the high hydrolysis rate of titanium isopropoxide, hydrolysis can be initiated in the presence of isopropanol, without any additional hydrolysis agent being needed. Inlet temperature is fixed at 130° C. and outlet at 80° C. Powder is recovered in the cyclone by adding a magnet inside the bowl.

Figure 20:
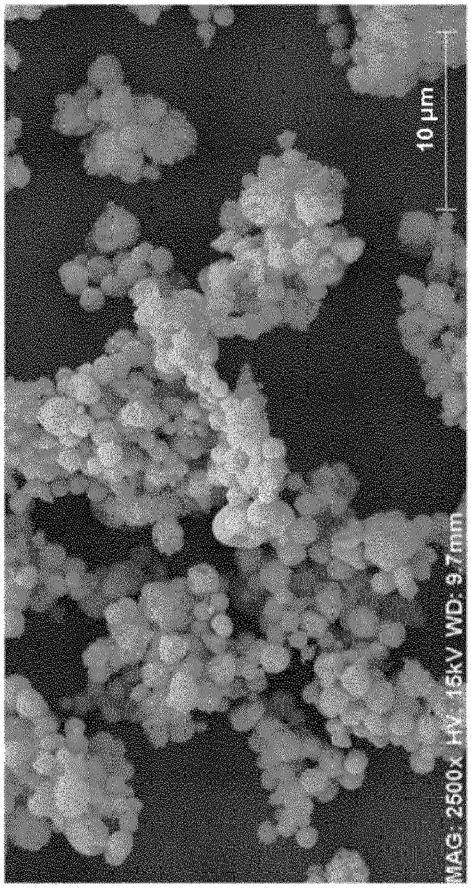
FIG. 20: SEM micrographs of core-shell particles with $TiO_2$, with $TiO_2$:$Fe_3O_4$ ratio of 0.683:1

FIG. 20 shows SEM micrograph of core shell particles $TiO_2$—$Fe_3O_4$ obtained using this process. Micrometric and weakly agglomerated spherical core-shell $TiO_2$—$Fe_3O_4$ particles were obtained. Specific surface area for $TiO_2$—$Fe_3O_4$ particles is about 204 $m^2/g$ and particle size is around 2.3 m with low size distribution (Table 7). Atomic ratio Ti/Fe in the final product can be controlled through the $TiO_2$:$Fe_3O_4$ weight ratio.

TABLE 7 particle size, specific surface area and atomic ratio Ti:Fe

| Weight ratio $TiO_2$:$Fe_3O_4$ | D0.5 (μm) | D0.9 (μm) | BET specific surface area ($m^2/g$) | Density (g/mL) | Atomic ratio Ti:Fe |
|---|---|---|---|---|---|
| 0.683:1 ($TiO_2$:$Fe_3O_4$) | 2.3 | 3.8 | 204 | 0.23 | 1.01:1 |

Example 7

In this example, core-shell particles were prepared in an identical manner as for example 1 except that powder was recovered in the cyclone without using a magnet for the recovery. Yield of production was of 45% when not using a magnet, compared to a yield up to 85% when using a magnet. Core-shell powders obtained by this process are characterized by a very low bulk density and particles size around 4.2 μm which may explain that less particles are recovered in the cyclone without using magnetization.

Example 8

The capacity of extraction of DNA or RNA using the core-shell particles obtained in example 1 was tested using extraction of *Escherichia* virus MS2 or Pneumonia Virus of mice (PVM). These particles were also successfully used for extraction of SARS-Cov-2 RNA gene (N gene, S gene et ORF1ab). KingFisher™ Flex Magnetic Particle Processor with 96 Deep-Well Head was used.

Preparation of the plates (Deepwell 96 plates) requested to wash each plate with 600 μl of buffer and then with 600 μl and 900 μl of ethanol 80%. Elution plate was prepared using 50 μl of elution buffer (TrisHCl 5 mM pH8).

Extraction of pneumovirus genomic RNA from mice containing the J3666 PVM, *Escherichia* virus MS2 or SARS-Cov-2 RNA was performed using a total volume of 350 μL (328 μl of commercial lysis buffer containing guanidine thiocyanate and 22 μl of Prot K 20 mg/ml). 100 μL of sample to each well of the 96 deepwell sample plate was added and incubated for 2 minutes at RT. 10 μL of commercial extraction control (Diagenode reference DICR-YD-L100 or DICR-CY-L100) were added to each sample well and to the Negative Control as well. 50 μl (15 mg/ml) of suspended in isopropanol magnetic core-shell particles produced as described in example 1 were added for each well and then 515 μl of isopropanol (98%) were added to each one.

RNA samples of SARS-Cov-2, MS2 or pneumovirus of mice (SH gene) were loaded on PCR plates and both and extraction control genomes were detected using Taqman-RT-q-PCR following manufacturer's recommendations. The volume of reactions was 20 μL. The amount of RNA was 4 μL. The data can be processed with the FastFinder software (v 3.300.3) and results released to GLIMS.

Figure 21:
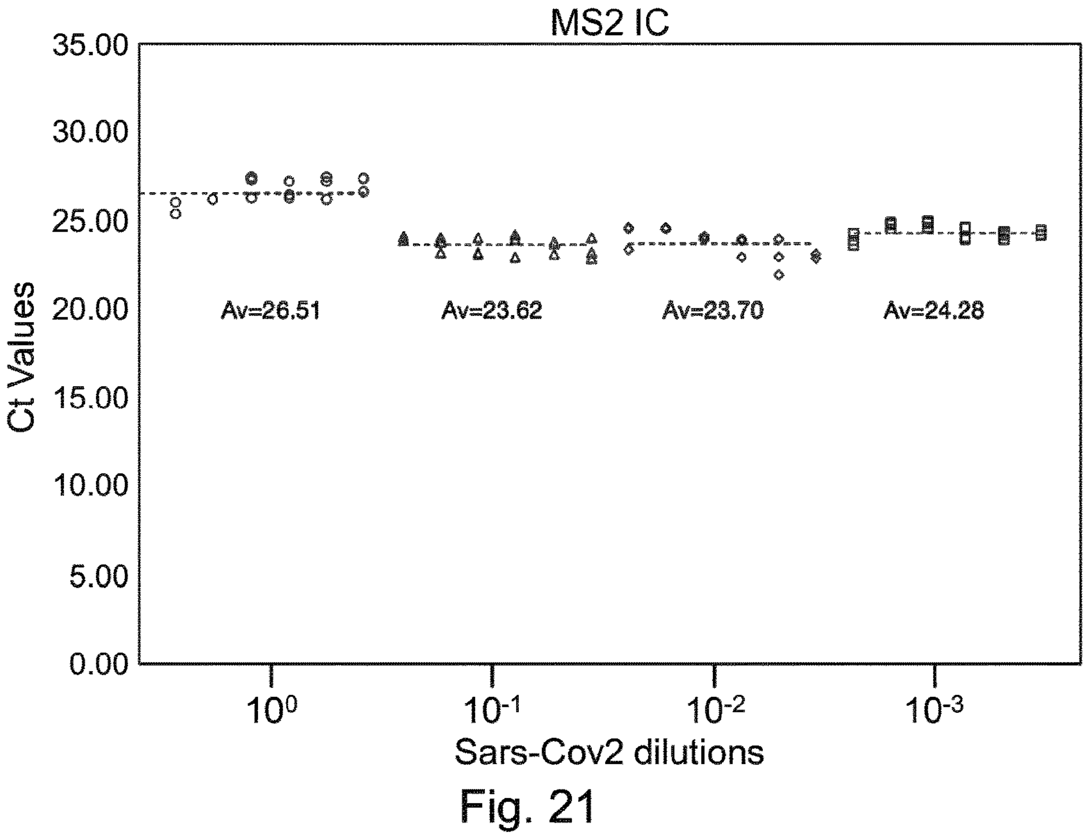
FIG. 21: Evolution of the cycle threshold (Ct) according to the concentration of MS2.

FIG. 21 shows the evolution of the cycle threshold (Ct) according to the concentration of MS2. This Ct value is representative of the number of cycles of extraction needed before a signal is obtained in the PCR method. The lower the number, the better the sensitivity of the sample is. A low number indicates a high sensitivity. The Ct value is the cycle number at which the sample becomes positive. This is the cycle number at which the signal becomes detectable. The signal detected may be a fluorescent signal. Commercially available magnetic particles may have a Ct value around 35. In this example, Ct is around 24 independently of the concentration of MS2. This indicates that the particles obtained by the present method are detected earlier in the extraction process, which is advantageous for this application.

Figure 22:
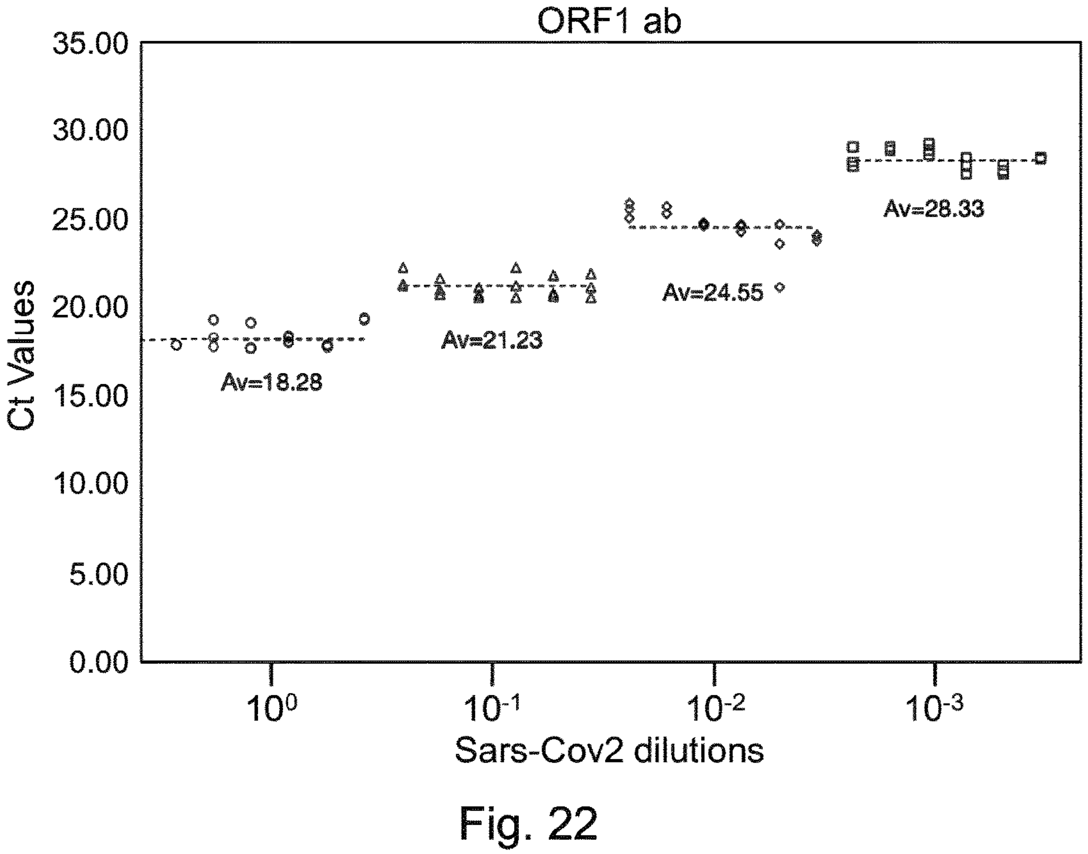
FIG. 22: Evolution of the Ct according to the concentration of ORF1 ab gene from SARS-Cov-2.
Figure 23:
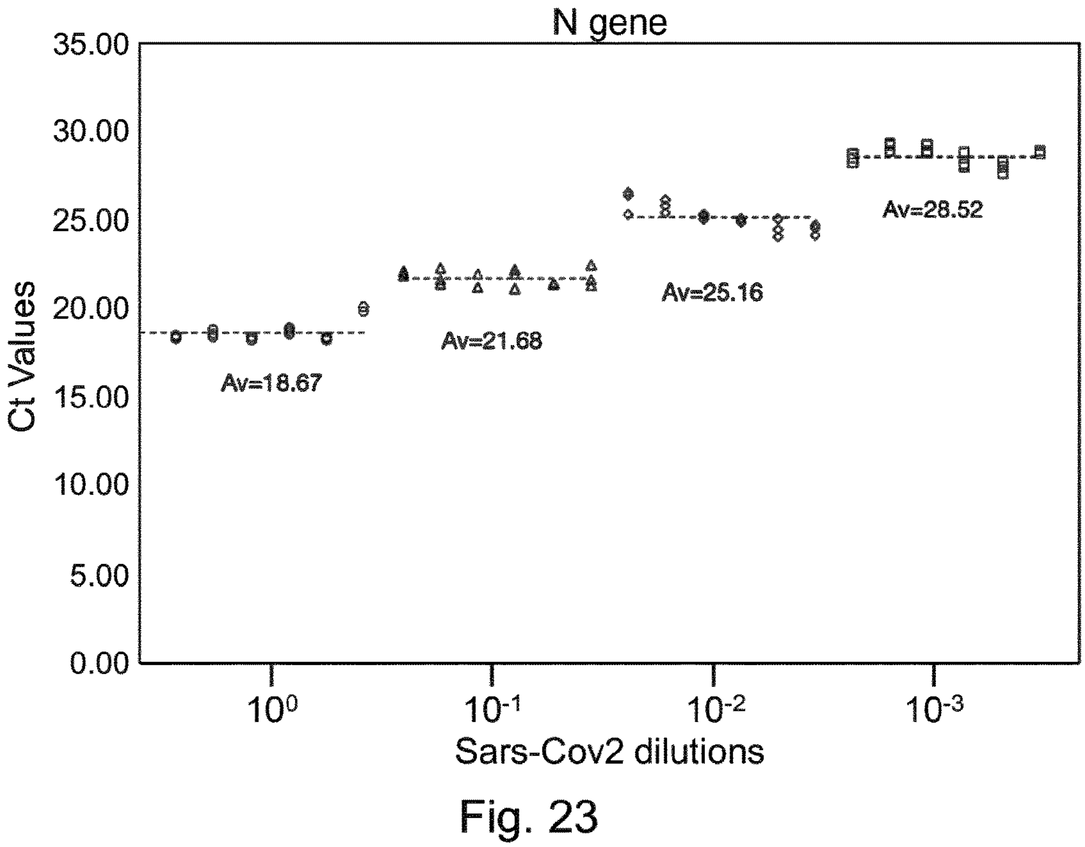
FIG. 23: evolution of the Ct according to the concentration of N gene from SARS-Cov-2.
Figure 24:
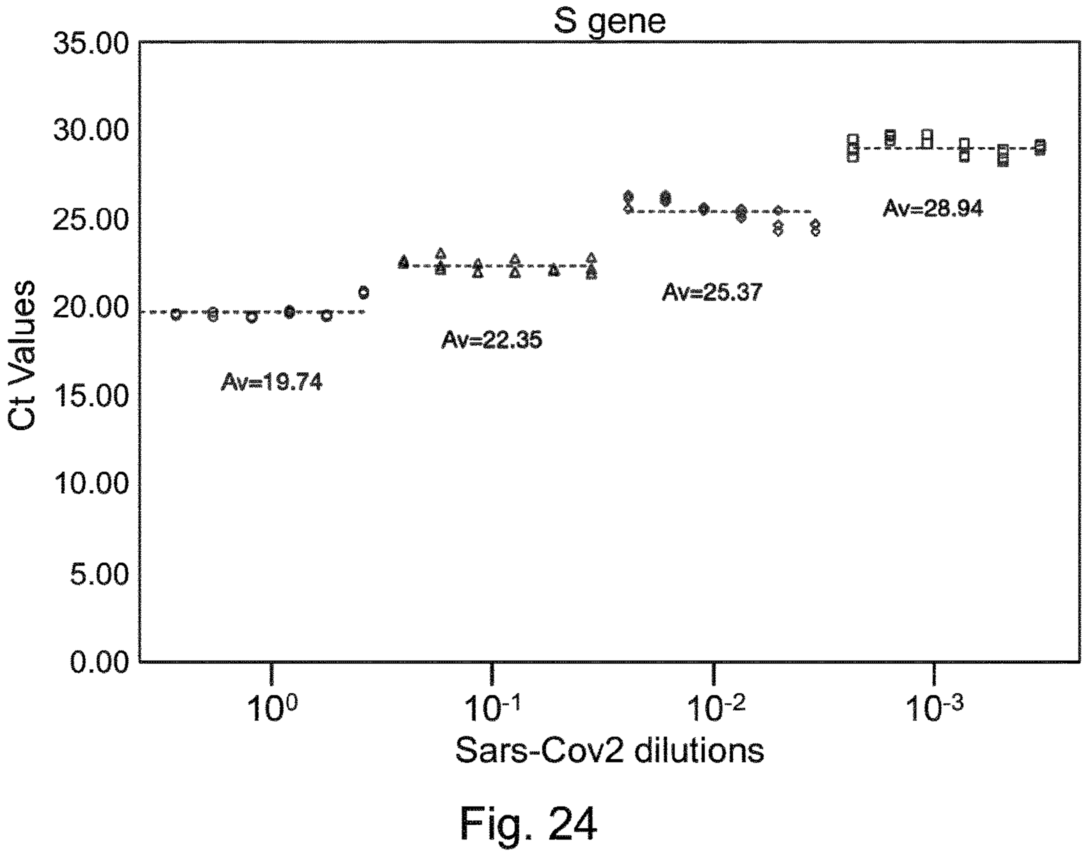
FIG. 24: Evolution of the Ct according to the concentration of N gene from SARS-Cov-2.

FIGS. 22 to 24 show the evolution of the cycle threshold (Ct) according to the concentration of respectively ORF1ab, N Gene and S Gene from SARS-Cov-2. Core-shell particles used allow for a good extraction of genes from SARS-Cov-2 with a very good sensitivity for each gene detected. Ct about 18.28, 21.23, 24.55 and 28.33 for dilutions of respectively of 1, 0.1, 0.01 and 0.001 is measured for ORF1ab gene. For N gene, Ct measured are 18.67, 21.68, 25.16 and 28.52 for dilutions of respectively of 1, 0.1, 0.01, 0.001. For N gene, Ct measured are 19.74, 22.35, 25.37 and 28.94 for dilutions respectively of 0.1, 0.01, 0.001.

Figure 25:
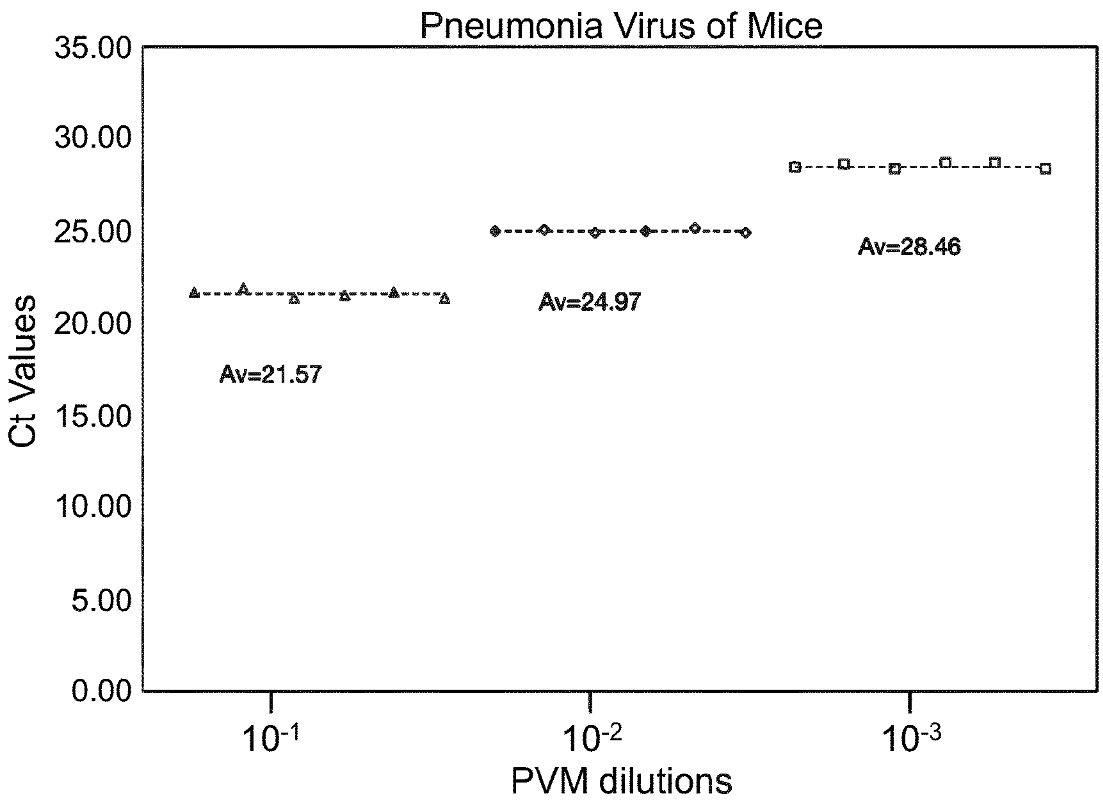
FIG. 25: Evolution of the Ct according to the concentration of pneumonia virus of mice (PVM).

FIG. 25 shows the evolution of the cycle threshold (Ct) according to the concentration of Pneumonia Virus of Mice (PVM). Ct measured are 21.57, 24.97 and 28.46 for dilutions of respectively of 0.1, 0.01, 0.001.

The invention claimed is:

1. A process for preparing core-shell particles comprising the steps of (i) providing a dispersion of primary magnetic particles having a mean diameter lower than 200 nm in a solvent;

(ii) adding at least one of a semi-metal oxide, a metal oxide, a semi-metal oxyhydroxide and a metal oxyhydroxide and/or at least one precursor of a semi-metal oxide, a metal oxide, a semi-metal oxyhydroxide and a metal oxyhydroxide to said dispersion;

(iii) optionally adding a hydrolysis agent for said one or more precursor(s); and (iv) injecting the dispersion in a spray dryer;

whereby a shell comprising at least one of a semi-metal oxide, a metal oxide, a semi-metal oxyhydroxide and a metal oxyhydroxide is formed on the magnetic particles during spray drying and wherein step (iv) is performed immediately or in a short period of at most 10 minutes after step (ii) or, when a hydrolysis agent is present, immediately or in a short period of at most 10 minutes after step (iii).

2. The process according to claim 1 wherein the primary magnetic particles are iron oxide particles.

3. The process according to claim 2 wherein the weight ratio of iron oxide to the combination of the at least one of a semi-metal oxide, a metal oxide, a semi-metal oxyhydroxide, or a metal oxyhydroxide in the dispersion is from 0.1:5 to 5:0.1.

4. The process according to claim 1 wherein the solvent is water or a solvent miscible with water used alone or in combination.

5. The process according to claim 1 wherein the at least one of a semi-metal oxide, a metal oxide, a semi-metal oxyhydroxide or a metal oxyhydroxide is silica, titanium oxide, aluminum oxide, zirconium oxide, pseudoboehmite, or zinc oxide.

6. The process according to claim 1 wherein the at least one of a semi-metal oxide, a metal oxide, a semi-metal oxyhydroxide or a metal oxyhydroxide is silica and/or the precursor thereof is a tetraalkyl orthosilicate, colloidal silica or a mixture of both.

7. The process according to claim 1 wherein the hydrolysis agent is an aqueous solution of a gaseous base.

8. The process according to claim 1 wherein the pressure of the spray dryer is about 1 bar.

9. The process according to claim 1 wherein the outlet temperature of the spray dryer is between 50° C. and 150° C.

10. The process according to claim 1 further including a step (v) of recovering a powder of magnetic particles coated by the at least one of a semi-metal oxide, a metal oxide, a semi-metal oxyhydroxide and a metal oxyhydroxide from an outlet of the spray dryer through magnetization.

11. Particles obtainable by the process as defined in claim 1 wherein the core-shell particles have a size in the range 1 to 20 μm and have a specific surface area from 30 $m^2$/g up to 120 $m^2$/g.

12. The particles according to claim 11 having a density of less than 0.5 g/ml.

13. A formulation comprising particles according to claim 11.

14. A method for RNA or DNA extraction comprising (i) providing a sample, (ii) optionally, treating the sample with a lysis buffer, (ii contacting RNA or DNA in the sample with the particles of claim 11, (iv) allowing the RNA or DNA in the sample to adsorb to the particles, and (v) optionally, eluting the contacted RNA or DNA from the particles.

* * * * *